US005235033A

United States Patent [19]

Summerton et al.

[11] Patent Number: 5,235,033

[45] Date of Patent: * Aug. 10, 1993

[54] ALPHA-MORPHOLINO RIBONUCLEOSIDE DERIVATIVES AND POLYMERS THEREOF

[75] Inventors: James E. Summerton; Dwight D. Weller; Eugene P. Stirchak, all of Corvallis, Oreg.

[73] Assignee: Anti-Gene Development Group, Corvallis, Oreg.

[ * ] Notice: The portion of the term of this patent subsequent to Jul. 23, 2008 has been disclaimed.

[21] Appl. No.: 454,056

[22] Filed: Dec. 20, 1989

Related U.S. Application Data

[63] Continuation-in-part of Ser. No. 100,033, Sep. 23, 1987, Pat. No. 5,142,047, which is a continuation-in-part of Ser. No. 944,707, Dec. 8, 1986, and a continuation-in-part of Ser. No. 911,258, Sep. 24, 1986, abandoned, and a continuation-in-part of Ser. No. 712,396, Mar. 15, 1985, abandoned.

[51] Int. Cl.[5] ...................... C08G 75/18; C08G 75/20; C08G 75/24; C07D 413/00

[52] U.S. Cl. .................................... 528/391; 528/403; 528/405; 528/406; 544/81; 544/82

[58] Field of Search .................... 544/81, 82; 528/391, 528/403, 405, 406

[56] References Cited

U.S. PATENT DOCUMENTS 4,558,047 12/1985 Takaya et al. ...................... 514/229
5,034,506 7/1991 Summerton et al. ............... 528/391

FOREIGN PATENT DOCUMENTS

WO9118898A 6/1990 Japan .
WO86/05518 9/1986 PCT Int'l Appl. .
WO86/05519 9/1986 PCT Int'l Appl. .

OTHER PUBLICATIONS

Stirchak et al., Nucleic Acids Research, vol. 17, No. 15, (1989), pp. 6129-6141.
Khym, J. X., Biochemistry 2 (2):334 (1963).
Mungall, W. S. et al., J. Org. Chem. 42 (4):703 (1977).
Tittensor, J. R., J. Chem. Soc. (C):2656 (1971).
Gait, M. J., et al., J. C. S. Perkins I:1684 (1974).
Jones, A. S., et al., Biochem. et Biphys. Acta 365:365 (1973).
Blake et al., Biochem, 24:6132 (1985a).
Blake et al., Biochem, 24:6139 (1985b).
Froehler, et al., Nucleic Acids Res. 16:4831 (1988).
Jayaraman, et al., Proc Natl Acad Sci USA 78:1537 (1981).
Miller, et al., Biochemistry 18:5134 (1979).
Miller, et al., J Biol Chem 255:6959 (1980).
Miller, et al., Biochimie 67:769 (1985).
Murakami, et al., Biochemistry 24:4041 (1985).
Pitha, Biochem Biphys Acta 204:39 (1970a).
Pitha, Bipolymers 9:965 (1970b).
Smith, et al., Proc Natl Acad Sci USA 83:2787 (1986).
Stirchak, E. P. et al., Organic Chem. 52:4202 (1987).

*Primary Examiner*—Mukund J. Shah
*Assistant Examiner*—Philip I. Datlow
*Attorney, Agent, or Firm*—Peter J. Dehlinger; Gary R. Fabian

[57] ABSTRACT

Alpha-morpholino subunits and polymer compositions composed of alpha-morpholino subunits are disclosed. These subunits can be linked together by uncharged linkages, one to three atoms in length, joining the morpholino nitrogen of one subunit to the 5' exocyclic carbon of an adjacent subunit. Each subunit contains a purine or pyrimidine base-pairing moiety effective to bind by hydrogen bonding to a specific base or base-pair in a target polynucleotide. The polymers of the present invention can be used in place of standard RNA or DNA oligomers for a number of standard laboratory procedures, for example, as probes in solid-phase systems and nucleic acid hybridization analyses. Further, the polymers of the present invention have potential use as therapeutic agents in anti-sense-type technologies.

16 Claims, 16 Drawing Sheets

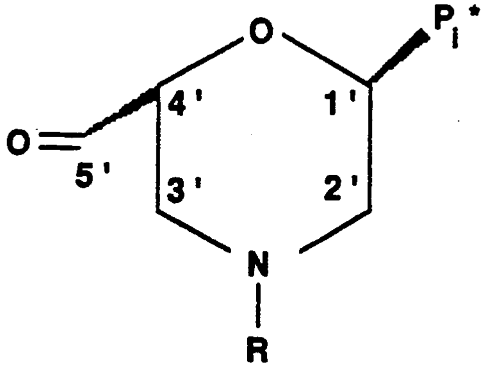
Fig 1
1.
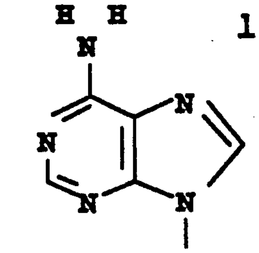
2.
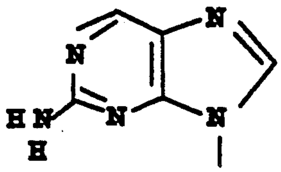
3.
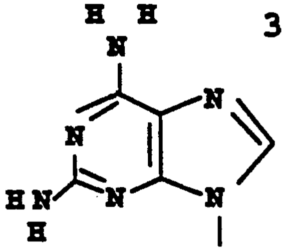
4.
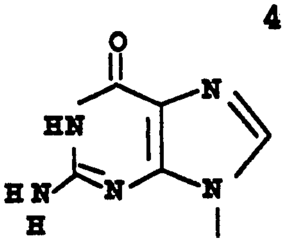
5.
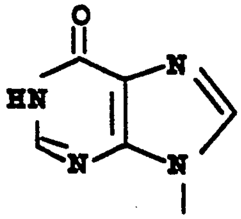
6.
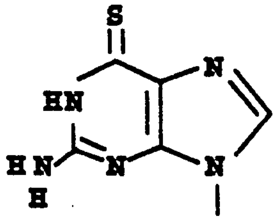
7.
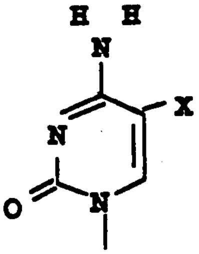
8.
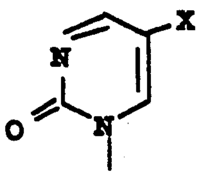
9.
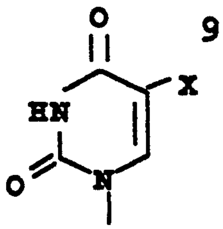
X= H, $CH_3$ , F, Cl, Br, I
Fig. 2

$X_1$ = O, S $X_2$ = O, S, $CH_2$, NR

R = H, $CH_3$, other alkyl or substituted alkyl

Y = O, S

Z = $CH_2R$, $OCH_2R$, $SCH_2R$, $NR_1R_2$ ($R_1$ & $R_2$ selected from R or comprise cyclic structure)

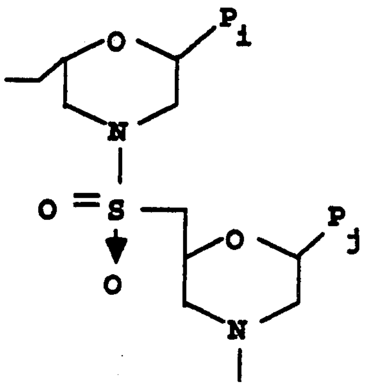
Fig. 4A-A
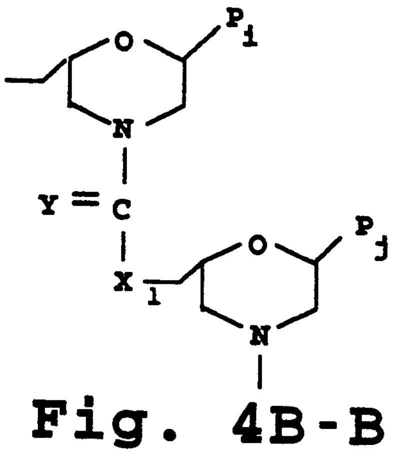
Fig. 4B-B
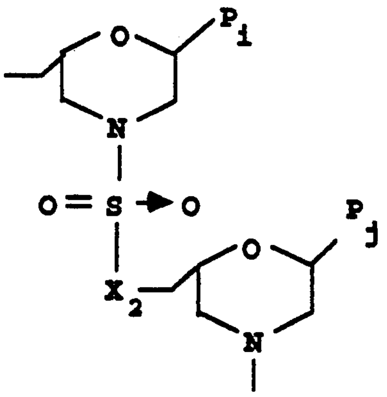
Fig. 4C-C
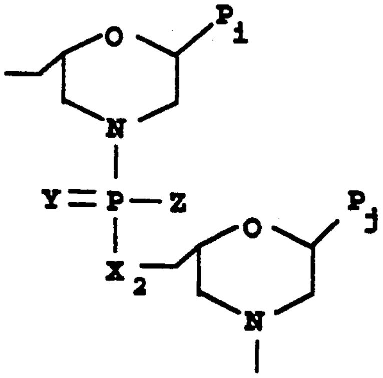
Fig. 4D-D

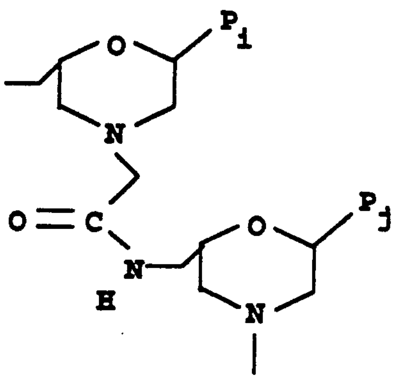
Fig. 4E-E
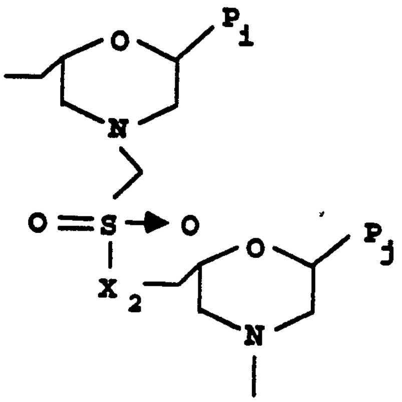
Fig. 4F-F
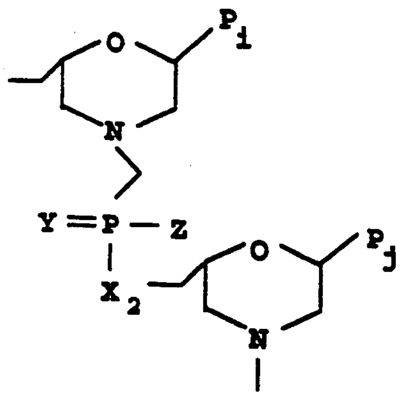
Fig. 4G-G

1

2

3

4

```
5'  GGDDDGGDDGucDGDDGGcDDDDD    Polymer
    ||||||||||::||||||:|||||
5'  ggaaaggaagtcagaaggcaaaaa    Target
3'  cctttccttcagtcttccgttttt    duplex
```

where:

a = adenine  | = high specificity bonding
c = cytosine  : = low-specificity bonding
g = guanine
t = thymine  D = 2,6-diaminopurine or 2-aminopurine
u = uracil  G = guanine or thioguanine

ALPHA-MORPHOLINO RIBONUCLEOSIDE DERIVATIVES AND POLYMERS THEREOF

This application is a continuation-in-part (CIP) of copending U.S. patent application Ser. No. 07/100,033, filed 23 Sep. 1987 now U.S. Pat. No. 5,142,047. Application Ser. No. 07/100,033 is a continuation-in-part of allowed U.S. patent application Ser. No. 06/944,707, filed 18 Dec. 1986, and a continuation-in-part of application Ser. No. 06/911,258, filed 24 Sep. 1986, now abandoned, and a continuation-in-part of application Ser. No. 06/712,396, 15 Mar. 1985, now abandoned.

This application was filed on even date with co-pending, co-owned U.S. patent application Ser. Nos. 07/454,057, now abandoned, and 07/454,055. Application Ser. No. 07/454,055 issued on 23 Jul. 1991 as U.S. Pat. No. 5,034,506. Application Ser. No. 07/799,681, now U.S. Pat. No. 5,185,444, is a File-Wrapper Continuation of U.S. patent application Ser. No. 07/454,057.

FIELD OF THE INVENTION

The present invention relates to morpholino-based polymers.

REFERENCES

Agarwal, Proc Nat Acad Sci USA, 85:7079 (1988).
Balgobin, N., et al., Tetrahedron Lett, 22:3667 (1981).
Belikova, Tetrahedron Lett, 37:3557 (1967).
Blake et al., Biochem, 24:6132 (1985a).
Blake et al., Biochem 24:6139 (1985b).
Bower et al., Nucleic Acids Research, 15:4915 (1987).
Dikshit et al., Canadian J Chem, 66:2989 (1988).
Ferrier, Carbohydrate Chem Biochem, 35:31 (1978).
Fild et al., Chem Ber, 113:142 (1980).
Froehler et al., Nucleic Acids Res. 16:4831 (1988).
Fox, J. J., et al., J Am Chem Soc, 80:1669 (1958).
Gait, "Oligonuoleotide Synthesis, A practical Approach," pages 31-33, IRL Press, Oxford, England (1984).
Goldberg, M. L., et al; Methods in Enzymology 68:206 (1979).
Greenlee, J Org Chem, 49 2632 (1984).
Grunstein, M., et al; Methods in Enzymology 68:379 (1979).
Himmelsbach, F., and Pfleiderer, W., Tetrahedron Lett, 24:3583 (1983).
Jayaraman et al., Proc Natl Acad Sci USA 78:1537 (1981).
Kamimura et al., Chemistry Letters (The Chem. Soc. of Japan) pg. 1051 (1983).
LaPlanche et al , Nucleic Acids Research, 14:9081 (1986).
Lerman, L. S., "DNA Probes: Applications in Genetic and Infectious Disease and Cancer," Current Comm in Molec Biol, Cold Spring Harbor Laboratory (1986).
McBride, et al., J Amer Chem Soc 108:2040 (1986).
Letsinger and Miller, J Amer Chem Soc, 91:3356 (1969)
Miller et al., Biochemistry 18:5134 (1979).
Miller et al., J Biol Chem 255:6959 (1980).
Miller et al., Biochimie 67:769 (1985).
Murakami et al., Biochemistry 24:4041 (1985).
Niedballa, U., and H. Vorbruggen, J Org Chem, 39:3668 (1974).
Pitha, Biochem Biophys Acta 204:39 (1970a).
Pitha, Biopolymers 9:965 (1970b).
Reese, C. B., and Saffhill, R. S., J Chem Soc Perkin Trans, 1:2937 (1972).
Smith et al., J Am Chem Soc, 80:6204 (1958)
Smith et al., Proc Natl Acad Sci USA 83:2787 (1986).
Southern, E.; Methods in Enzymology 68:152 (1979)
Stirchak E. P. et al., Organic Chem. 52:4202 (1987).
Summerton et al., J Molec Biol, 122:145 (1978).
Summerton et al , J Theor Biol, 78:61 (1979a).
Summerton, J Theor Biol, 78:77 (1979b)
Szostak, J. W., et al, Methods in Enzymology 68:419 (1979).
Thomas, P.; Methods in Enzymology 100:255 (1983)
Toulme et al., Proc Nat Acad Sci, USA 83:1227 (1986).
Trichtinger et al., Tetrahedron Letters 24:711 (1983).

BACKGROUND OF THE INVENTION

Polymers which are designed for base-specific binding to polynucleotides have significant potential both for in vitro detection of specific genetic sequences characteristic of pathogens (Lerman) and for in vivo inactivation of genetic sequences causing many diseases—particularly viral diseases (Belikova, Summerton).

Standard ribo- and deoxyribonucleotide polymers have been widely used both for detection of complementary genetic sequences, and more recently, for inactivating targeted genetic sequences. However, standard polynucleotides suffer from a number of limitations when used for base-specific binding to target oligonucleotides. These limitations include (i) restricted passage across biological membranes, (ii) nuclease sensitivity, (iii) target binding which is sensitive to ionic concentration, and (iv) susceptibility to cellular strand-separating mechanisms.

In principle, the above limitations can be overcome or minimized by designing polynucleic acid analogs in which the bases are linked along an uncharged backbone. Examples of uncharged nucleic acid analogs have been reported. Pitha et al (1970a, b) have disclosed a variety of homopolymeric polynucleotide analogs in which the normal sugar-phosphate backbone of nucleic acids is replaced by a polyvinyl backbone. These nucleic acid analogs were reported to have the expected Watson/Crick pairing specificities with complementary polynucleotides, but with substantially reduced Tm values (Pitha, 1970a). One serious limitation of this approach is the inability to construct polymers by sequential subunit addition, for producing polymers with a desired base sequence. Thus the polymers cannot be used for base-specific binding to selected target sequences.

Polynucleotide analogs containing uncharged, but stereoisomeric, methylphosphonate linkages between the deoxyribonucleoside subunits have been reported (Miller, 1979, 1980; Jayaraman; Murakami; Blake, 1985a, 1985b; Smith, 1986). More recently a variety of analogous uncharged phosphoramidate-linked oligonucleotide analogs have also been reported (Froehler, 1988). These polymers comprise deoxynucleosides linked by the 3'OH group of one subunit and the 5'OH group of another subunit via an uncharged chiral phosphorous-containing group. These compounds have been shown to bind to and selectively block single-strand polynucleotide target sequences. However, uncharged phosphorous-linked polynucleotide analogs of the type just described have limitations, particularly the cost and difficulty of preparing the polymers.

More recently, deoxyribonucleotide analogs having uncharged and achiral intersubunit linkages have been constructed (Stirchak 1987). These uncharged, achiral deoxyribonucleoside-derived analogs, however, are limited by the relatively high cost of starting materials.

SUMMARY OF THE INVENTION

It is a general object Of the invention to provide subunits which can be prepared from relatively inexpensive starting materials and which can easily be assembled under relatively nonstringent reaction/protection conditions into polymers capable of sequence-specific binding to polynucleotides.

The invention includes an alpha-morpholino ribonucleoside derivative of the form:

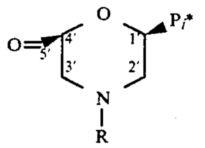

This alpha morpholino includes a purine or pyrimidine base-pairing moiety, $P_i$, which is effective to bind by base-specific hydrogen bonding to a base in a target sequence in a polynucleotide. It also includes an R group which comprises a hydrogen or a substituted alkyl group which can easily be cleaved or which contains a moiety suitable for linking to another subunit.

This derivative can readily be transformed into subunits having an alcohol, a sulfhydryl, an amine, or an electrophile at the 5′ position. Such subunits can be linked together by uncharged linkages, one to three atoms long, joining the morpholino nitrogen of one subunit to the 5′ carbon of another subunit, to give polymers suitable for binding complementary polynucleotide sequences.

These and other objects and features of the invention will become more fully apparent when the following detailed description of the invention is read in conjunction, with the accompanying examples and figures.

BRIEF DESCRIPTION OF THE FIGURES

FIG. 1 shows the alpha-morpholino ribonucleoside derivative;

FIG. 2 shows several exemplary purine- and pyrimidine base-pairing moieties (represented as Pi of the ring structures shown in FIG. 1);

FIG. 4 shows a repeating subunit segment of exemplary alpha-morpholino-based polymers, designated A—A through G—G;

DETAILED DESCRIPTION OF THE INVENTION

The present invention includes a morpholino ribonucleoside derivative having an aldehyde at the 5′ position (numbered as shown in FIG. 1) in the alpha orientation. The aldehyde of this morpholino can be converted to an alcohol, a sulfhydryl, an amine, or an electrophilic moiety retaining the same stereochemical orientation. Polymers can be assembled from these alpha-morpholino subunits, where the subunits are connected by uncharged linkages one to three atoms long which join the morpholino nitrogen of one subunit to the 5′ carbon of another subunit.

A. Morpholino-Based Subunits

FIG. 1 shows the morpholino ring structures on which the polymer subunits are based, where the morpholino carbon atoms are numbered as shown. As seen in FIG. 1, the ring structure contains a 5′ carbon attached to the 4′ carbon in the α-orientation.

Each ring structure includes a purine, pyrimidine, or related hydrogen-bonding moiety, $P_i$, attached to the backbone-morpholine moiety through a linkage in the β-orientation.

The purine hydrogen-bonding moieties or bases include purines as well as purine-like planar ring structures having a 5–6 fused ring in which one or more of the atoms, such as N3, N7, or N9 is replaced by a suitable atom, such as carbon. The pyrimidine moieties likewise include pyrimidines as well as pyrimidine-like planar 6-membered rings in which one or more of the atoms, such as N1, is replaced by a suitable atom, such as carbon. Preferred hydrogen-bonding moieties in the invention include the set of purines and pyrimidines shown in FIG. 2. Each base includes at least two hydrogen-bonding sites specific for a polynucleotide base or base-pair. Where the polymers are used for sequence-specific binding to single-stranded polynucleotides, the purine structures 1–3 are designed to bind to thymine or uracil bases; structures 7–8, to guanine bases; structures 4–6, to cytosine bases; and structure 9, to adenine bases.

The polymers of the invention are also effective to bind to hydrogen-bonding sites accessible through the major-groove in duplex polynucleotides having mostly purine bases in one strand and mostly pyrimidine bases in the complementary strand, as discussed below.

Figures 8A, 8B:
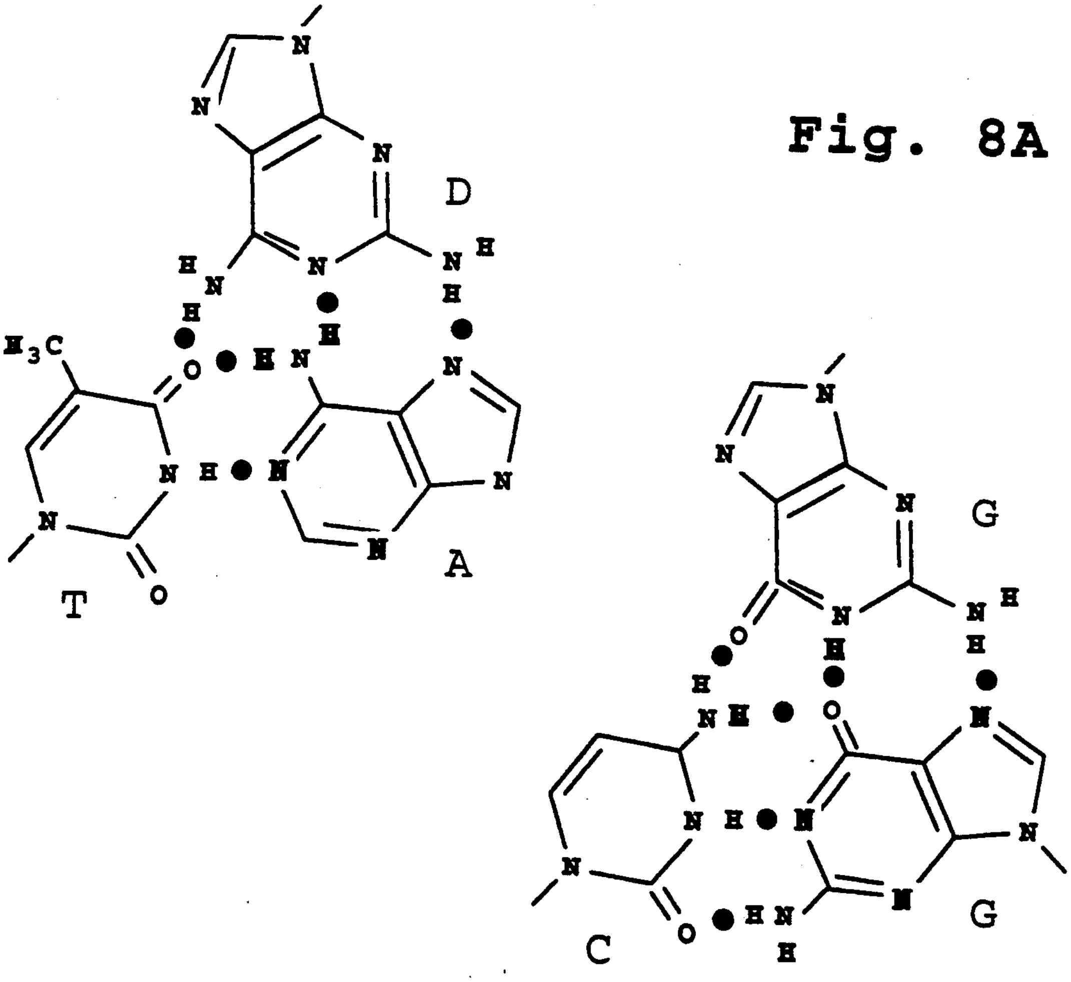
FIG. 8A shows the binding mode for 2-amine-containing purines to polar major-groove sites of respective target base-pairs.
FIG. 8B illustrates a representative base sequence of a duplex-binding polymer.

Because of the similar type and positioning of the two central polar major-groove sites among the different base-pairs of duplex nucleic acids (i.e., the NH4 and O6 of a CG base-pair present the same H-bonding array as the NH6 and O4 of an AT base-pair), the H-bonding moiety of a duplex-binding polymer must hydrogen-bond to the N7 of its target base-pair in order to uniquely recognize a given oriented base-pair in a target genetic duplex. Thus, where the polymers of the present invention are targeted against duplex genetic sequences (containing predominantly purines in one strand and predominantly pyrimidines in the other strand), the hydrogen-bonding moieties of the polymer preferably contain purines having an amine at the 2 position since that amine is suitably positioned for H-bonding to the N7 of the target base-pair. Structures 2 and 3 of FIG. 2 provide for specific binding to a TA or UA base-pair, and Structures 4 and 6 provide for specific binding to a CG base-pair. Two bases which are particularly useful in a duplex-binding polymer are 2,6-diaminopurine (Structure 3) and guanine (Structure 4). FIG. 8A illustrates the binding of these two bases to the polar major-groove sites of their respective target base-pairs in duplex nucleic acids.

The morpholino subunits of the instant invention are combined to form polymers by linking the subunits through stable, uncharged linkages. The linking group of a subunit usually includes a carbonyl-, sulfonyl-, or phosphorous-containing electrophile for reaction with a nucleophile of the subunit to which it is to be linked. As used herein "carbonyl" means a —C═O or —C═S group, and "sulfonyl" means an O═S→O group.

The selection of subunit linking groups for use in polymer synthesis is guided by several considerations. Initial screening of promising intersubunit linkages (i.e., those linkages which were predicted to not be unstable and which allow either free rotation about the linkage or which exist in a single conformation) typically involves the use of space-filling CPK or computer molecular models of duplex DNA or RNA. The DNA and RNA duplexes are constructed according to parameters determined by x-ray diffraction of oligodeoxyribonucleotides in the B-form and oligoribonucleotide-containing duplexes in the A-form.

In each of these constructed duplexes, one of the two sugar phosphate backbones is removed, and the prospective backbone, including the morpholino ring and intersubunit linkage, is replaced, if possible, on the sites of the bases from which the original sugar-phosphate backbone has been removed. Each resulting polynucleotide/polymer duplex is then examined for coplanarity of the Watson/Crick base pairs, torsional and angle strain in the prospective binding polymer backbone, degree of distortion imposed on the nucleic acid strand, and interstrand and intrastrand nonbonded interactions.

In the case of amide-containing linkages, special attention is paid to whether or not amide-containing backbones can readily adopt a conformation in which the amide moieties are planar. This is important because of the substantial energy cost required to force an amide into a nonplanar conformation.

Initial studies of this type carried out in support of the present invention showed that for morpholino-based polymers the preferred unit backbone length (i.e., the number of atoms in a repeating backbone chain in the polymer) is 6 atoms. However, the modeling studies also show that certain 5-atom and 7-atom repeating-unit morpholino-based backbones meet the requirements for binding to targeted genetic sequences.

Since the morpholino structure itself contributes 4 atoms to each repeating backbone unit, the linkages in the five-atom, six-atom, and seven-atom repeating-unit backbone contribute one, two, and three atoms to the backbone length, respectively. In all cases, the linkage between the ring structures is (a) uncharged, (b) stable, and (c) must permit adoption of a conformation suitable for binding to the target polynucleotide.

Subunit backbone structures judged acceptable in the above modeling studies were then assessed for feasibility of synthesis. The actual chemical stability of the intersubunit linkage was assessed with model compounds or dimers.

FIG. 3 shows several preferred morpholino subunit types, including linkage groups, which meet the requirements outlined above. A polymer constructed from these subunits may contain more than one linkage type.

Subunit A in FIG. 3 contains a 1-atom sulfonyl linkage which forms the five atom repeating-unit backbone shown at A—A in FIG. 4, where the morpholino rings are linked by a 1-atom sulfonamide linkage The corresponding amide linkage, substituting a carbonyl for sulfonyl linkage is not acceptable due to lack of rotational freedom about the carbon-nitrogen tertiary amide bond.

Subunits B, C and D in FIG. 3 are designated for 6-atom repeating-unit backbones, as shown at B—B, C—C, and D—D, respectively, in FIG. 4. In Structure B, the atom X linking the 5′ morpholino carbon to the carbonyl group may be oxygen or sulfur but not nitrogen or carbon, due to lack of free rotation about the resultant intersubunit linkage. The C═Y carbonyl group may be either C═O or C═S.

In Structure C in FIG. 3, the moiety X linking the 5′ morpholino carbon to the sulfonyl (O═S→O) group may be a methylene, oxygen, sulfur, or a nitrogen. The nitrogen may be secondary (NH), or tertiary (NR), where R is a methyl or other group which does not interfere with polymer binding to the target polynucleotide (as can be easily determined from molecular modeling studies such as those outlined above).

In Structure D in FIG. 3, the X moiety is as in Structure C, the Y moiety is oxygen or sulfer, and the Z moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, (including cyclic structures). Several cyclic disubstituted nitrogen moieties which are suitable for the Z moiety are morpholine, pyrrole, and pyrazole.

Subunits E-G in FIG. 3 are designed for 7-atom repeating-unit backbones, as shown at E—E through G—G, respectively, in FIG. 4. In Structures F and G, the X, Y and Z moieties are as in Structures C and D, respectively.

Based on the molecular modeling studies of the type described above, both the sulfamate (Structure C—C of FIG. 4 where X is oxygen) and sulfonate (Structure F—F of FIG. 4 where X is oxygen) linkages were good candidates for effective nucleic acid binding polymers. Experiments conducted in support of the present invention indicated that the 5′ tosylate of the basic morpholino cytosine subunit (Structure 4 of FIG. 6, where Pi is N4-benzoylated cytosine) are surprisingly resistant to both intermolecular and intramolecular nucleophilic attack on the 5′ methylene. This suggested that the corresponding sulfamate, and possibly the sulfonate also, may be sufficiently stable for intersubunit linkages. Accordingly, a sulfamate-linked dimer (Structure C—C of FIG. 4, where X is oxygen) was prepared, and assessed for linkage stability under conditions commonly used for polymer synthesis (i.e., detritylation conditions, base-deprotection conditions, and purification conditions, such as detailed in Examples 12 and 13).

These studies confirmed that such linkages are adequately stable under conditions typically required for synthesis, deprotection, purification and various applications.

B. Subunit Synthesis

The most economical starting materials for the synthesis of α-morpholino-subunits are generally ribonucleosides. Typically, ribonucleosides containing hydrogen-bonding moieties or bases (e.g., A, U, G, C) are transformed to their morpholino derivatives to provide a complete set of subunits for polymer synthesis. Where a suitable ribonucleoside is not available, a 1-haloribose or, preferably, a 1α-bromoglucose derivative, can be linked to a suitable base and this nucleoside analog then converted to the desired α-morpholino structure by essentially the same steps as outlined in Examples 2 and 3.

Because of the reactivity of the compounds used for subunit synthesis, activation, and/or coupling, it is generally desirable, and often necessary, to protect the exocyclic ring nitrogens of the bases and sometimes the oxygens of U and G. Selection of these protective groups is determined by (i) the relative reactivity of the moiety to be protected, (ii) the type of reactions involved in subunit synthesis and coupling, and (iii) the stability of the completed polymer prior to base deprotection.

Methods for base protecting a number of the more common ribonucleosides are given in Example 1. The methods detailed in the example are generally applicable for forming nucleosides with amine-protected groups. Standard base-protective groups used for nucleic acid chemistry are often suitable including the following groups: benzoyl for the N4 of cytosine (C); benzoyl or p-nitrobenzoyl for the N6 of adenine (A); acetyl, phenylacetyl or isobutyryl for the N2 of guanine (G); and N2,N6-bisisobutyryl for 2,6-diaminopurine residues. These protective groups can be removed after polymer assembly by treatment with ammonium hydroxide.

It is sometimes desirable to protect the base portion of the morpholino subunit with a group which can be readily removed by other than a nucleophilic base. Suitable base protective groups removable by a strong non-nucleophilic base via a β-elimination mechanism include 2-(4-nitrophenyl)ethoxy carbonyl or 2-(phenyl sulfonyl)ethoxycarbonyl for both the N4 of C and the N6 of A; and the 9-fluorenyl methoxycarbonyl for the N2 of G and the N2 and N6 of 2,6-diaminopurine. These groups can be removed after polymer assembly by treatment with the strong nonnucleophilic base 1,8-diazabicyclo[5.4.0]undec-7-ene (DBU), under stringently anhydrous conditions.

Figure 3A:
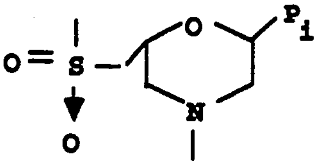
FIG. 3 shows several preferred subunits having linking groups suitable for forming polymers having five-atom (A), six-atom (B-D), and seven-atom (E-G) unit-length backbones.
Figure 3B:
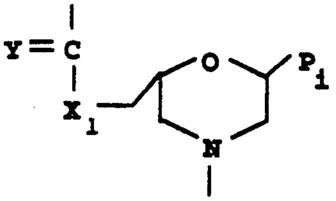
Figure 3C:
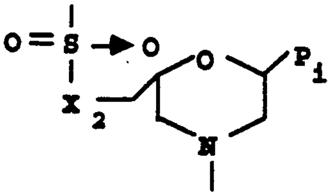
Figure 3D:
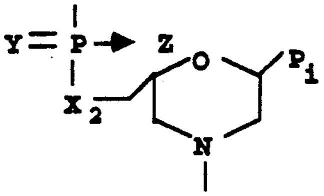
Figure 3E:
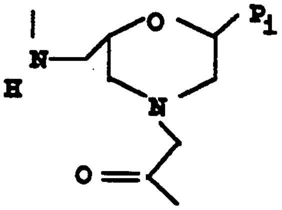
Figure 3F:
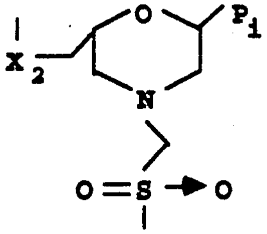
Figure 3G:
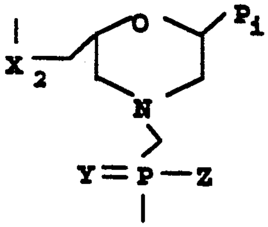
Figure 5:
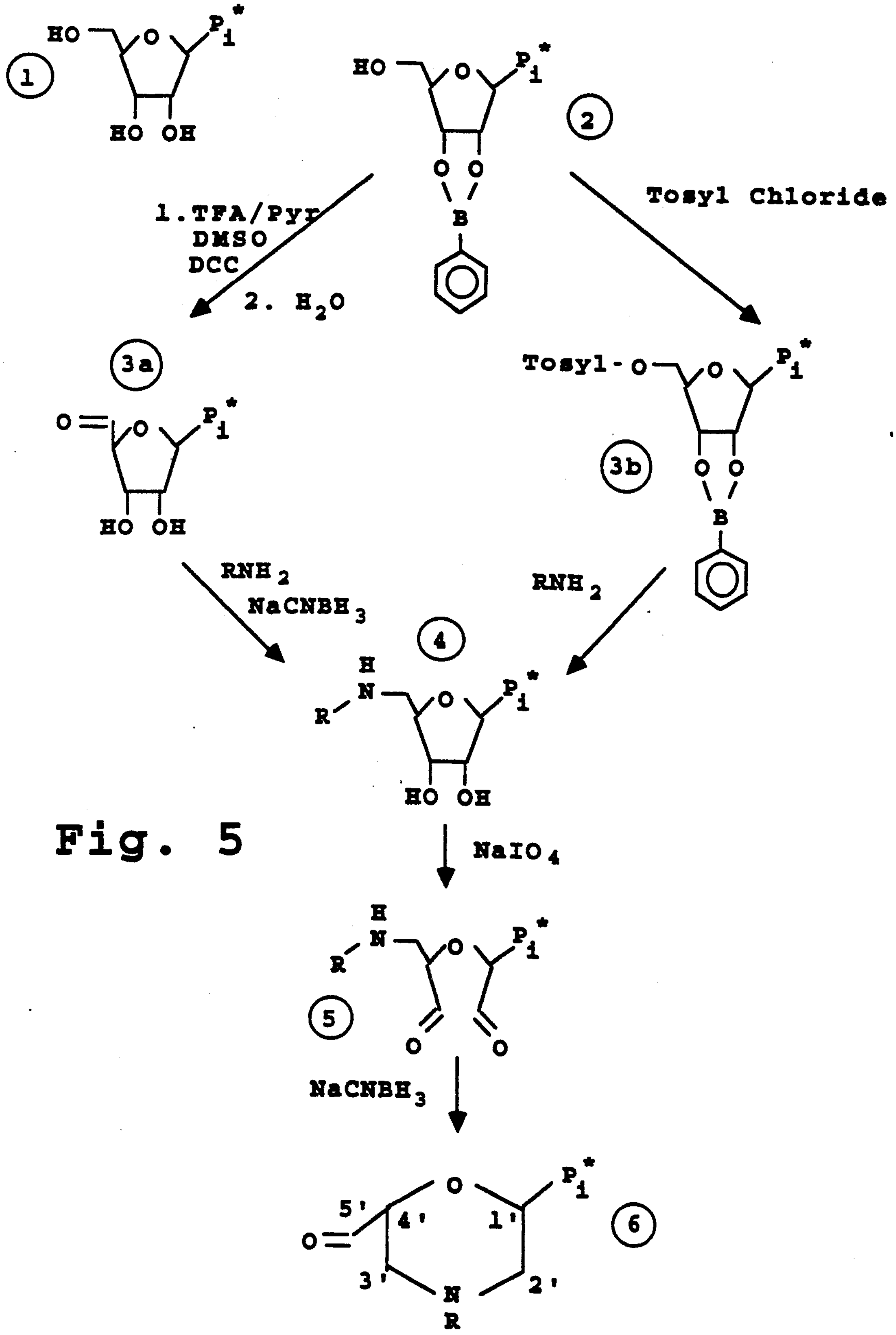
FIG. 5 shows the steps in the synthesis of the basic alpha-morpholino ribonucleoside derivative.

The synthesis of an alpha-mopholino ribonucleoside derivative is described in Examples 2 and 3 and illustrated in FIG. 5. Briefly, the 2′ and 3′ hydroxyls of a base-protected ribonucleoside are protected as phenylborate or acetonide derivatives. The 5′ hydroxyl in the beta orientation is then oxidized to an aldehyde and reductively converted to a primary or secondary amine. Alternatively, the 5′ hydroxyl is tosylated and then reacted with ammonia or a primary amine.

Figure 6:
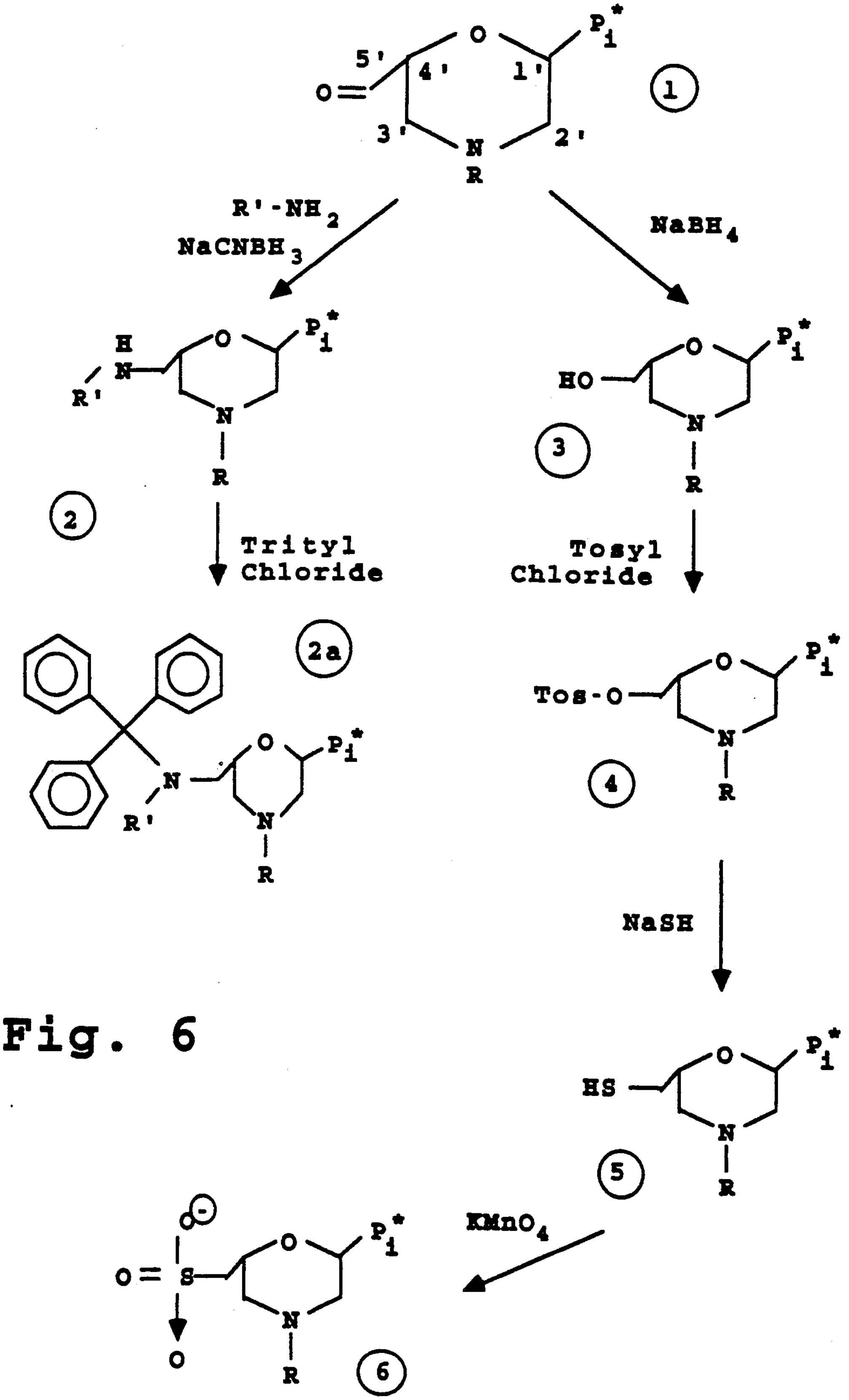
FIG. 6 illustrates conversion of the alpha-morpholino ribonucleoside derivative to useful subunit structures.

The ribose ring is then opened by treatment with sodium periodate to form a transient 2′-3′-dialdehyde. In the presence of sodium cyanoborohydride this dialdehyde closes on the amine linked to the 5′ carbon This closure forms a morpholino ring having a 5′ aldehyde in the alpha orientation (FIG. 1). The 5′ aldehyde can then be converted to a variety of linkable groups as illustrated in FIG. 6 and described in Example 4.

In the above morpholino synthesis, best results are obtained when the reaction solution is maintained near neutrality during the oxidation and morpholino ring closure reactions. This can be accomplished by continually titrating the reaction mix or, more conveniently, by using p-nitrophenol or benzotriazole as buffer. When the solution is too acidic the yield of product is low. When the solution is too basic, side products, possibly due to epimerization of the 1′ and/or 4′ carbons, are produced which are difficult to separate from the desired product. The reducing agent can be added before, during, or after the oxidation step with little noticeable effect on product yield.

The initial derivatives formed by the above methods contain a 5′-aldehyde in the α orientation and an R group on the morpholino ring nitrogen.

When the initial 5′ beta-aldehyde or beta-tosylate of the ribonucleoside is reacted with ammonia, the resultant R group on the morpholino ring nitrogen is a hydrogen. Alternatively, a cleavable R group is generated by reacting the initial 5′ beta aldehyde or tosylate with glycine, aminomethanesulfonic acid, or aminomethanephosphonic acid.

The 5′ alpha-aldehyde of the ribonucleoside derivative shown in FIG. 1 is then converted to an amine, hydroxyl, sulfhydral, or sulfonate moiety, as illustrated in FIG. 6 and described in Example 4. This results in a subunit structure suitable for coupling to a second morpholino subunit.

C. Activation and Coupling Reactions

The subunits prepared as above are coupled, in a controlled, sequential manner, generally by activating the carbonyl-, sulfonyl-, or phosphorous-containing group on one subunit and contacting this activated subunit with another subunit having an unprotected amine, hydroxyl, or sulfhydral. Different types of linkages may be employed in the construction of a single polymer.

Figure 9:
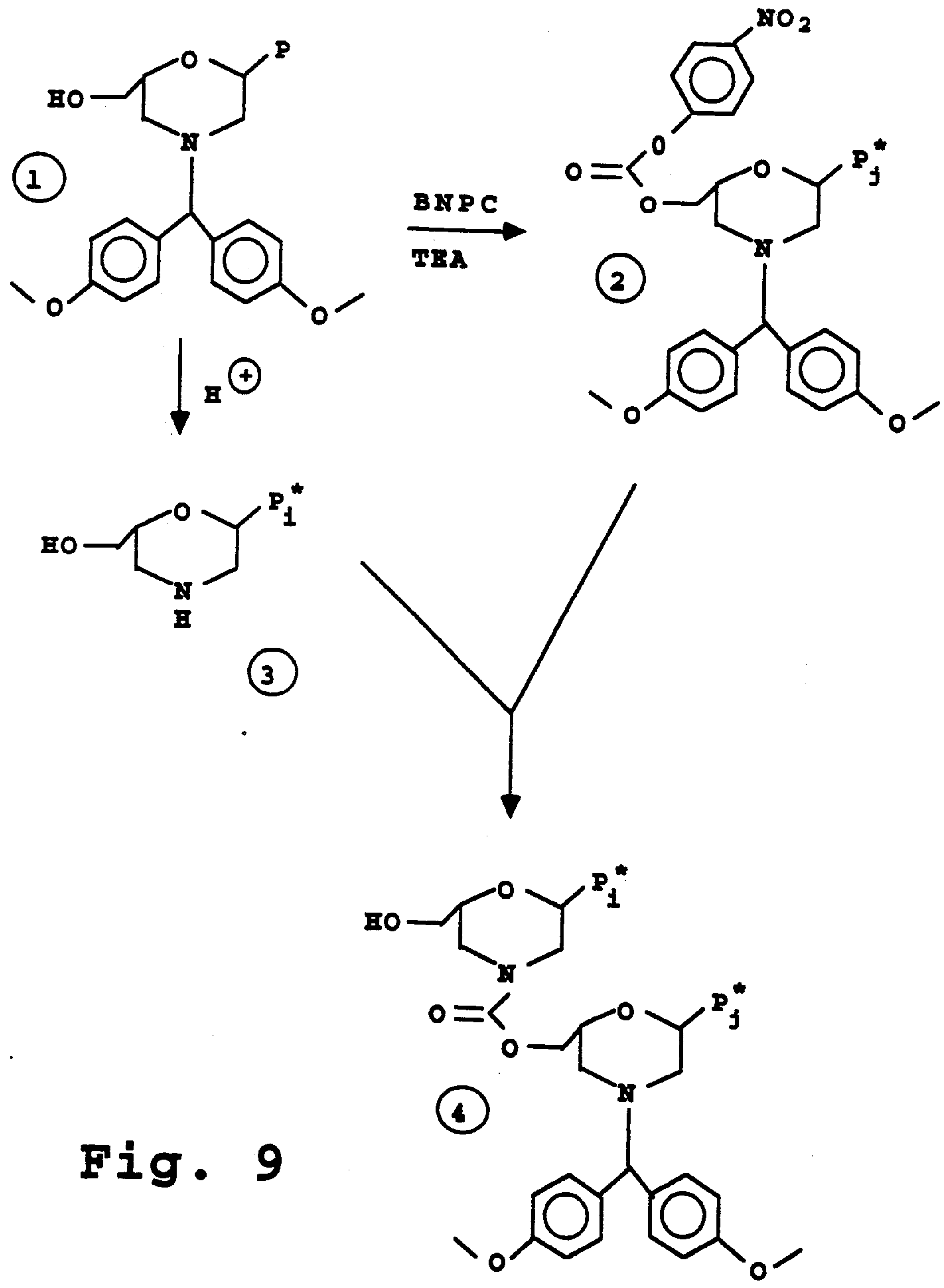
FIG. 9 shows the steps in linking two subunits through a carbamate linkage (B—B)

A number of closely related variations are possible for the carbonyl-containing linkages giving six-atom backbones, corresponding to Structure B—B in FIG. 4. A typical activation and coupling reaction for forming a carbamate linkage (where X is O in Structure B—B) is illustrated in FIG. 9. Here a base-protected morpholino subunit with a 5′-OH is reacted with bis-(p-nitrophenyl)carbonate and triethylamine to yield an activated carbonyl subunit (Structure 2, FIG. 9). This activated subunit is then combined with a second base-protected morpholino subunit which may be blocked at the 5′-OH. Bond formation between the subunits occurs between the annular nitrogen on the morpholino ring of subunit 2 and electrophilic carbonyl group of the first subunit, to form a carbamate linkage, where the carbonyl group is C=O. Details of the coupling reaction are given in Example 6.

Activation of the 5′-OH α-morpholino subunit with p-nitrophenylchlorothioformate and coupling to a second subunit with an unprotected ring nitrogen yields a thiocarbamate linkage (where Y is S in structure B—B of FIG. 4).

Figure 7:
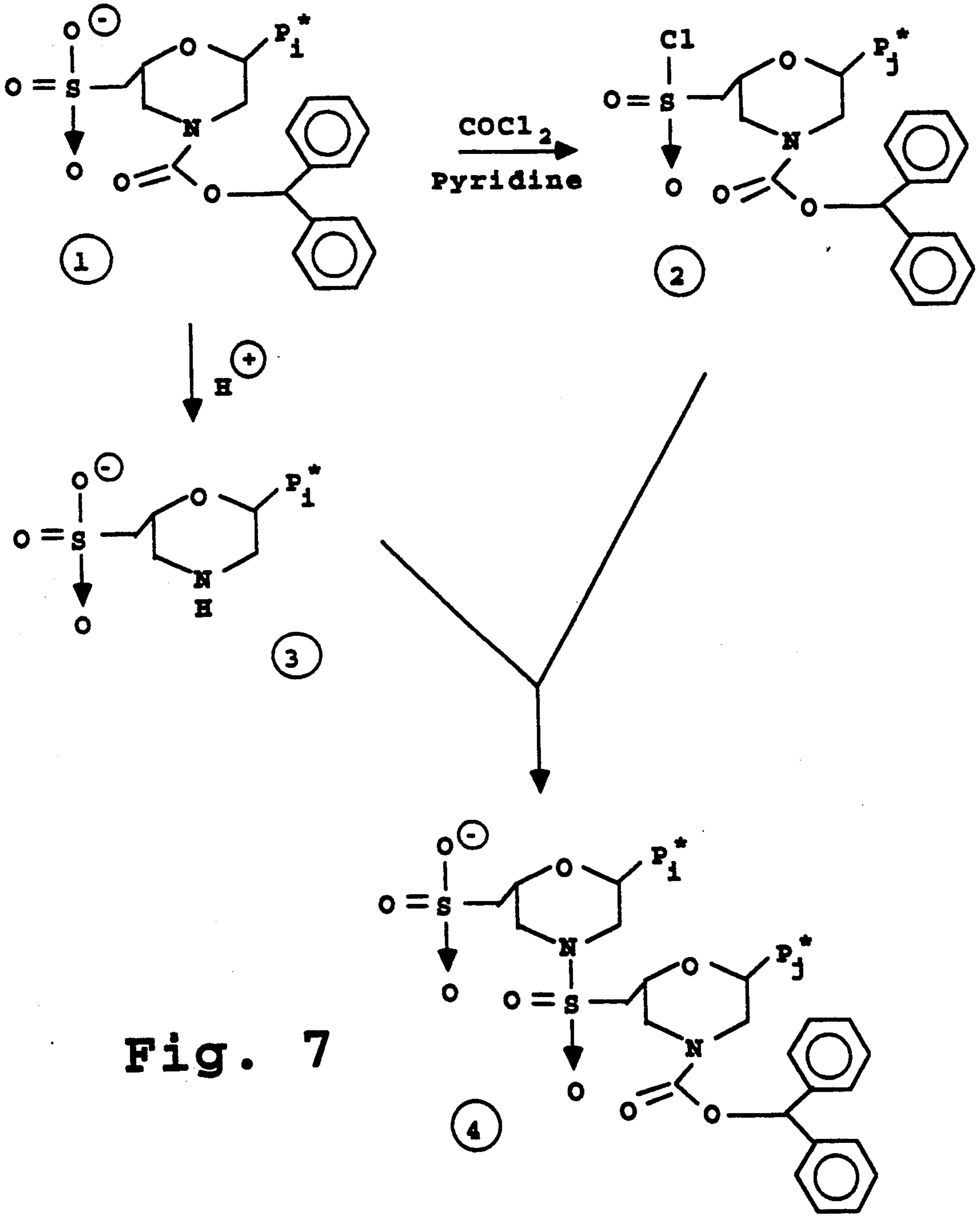
FIG. 7 shows the steps in linking two subunits through linkage A—A (FIG. 4)

The linkage in structure A—A in FIG. 4 (five-atom backbone) can be formed according to the reaction scheme shown in FIGS. 6 and 7, and detailed in Examples 4 and 5. Briefly, a 5′-OH morpholino subunit, protected at its ring nitrogen, is converted to a 5'SH subunit, then oxidized to convert the 5'-linked sulhydral group to a sulfonate group. The sulfonate group is activated with phosgene, and coupled to a second subunit having an unprotected ring nitrogen, as shown in FIG. 7 and described in Example 5. The polymer assembly is continued by deprotecting the morpholino ring nitrogen of the dimer, and reacting the dimer with a third activated subunit.

Figure 10:
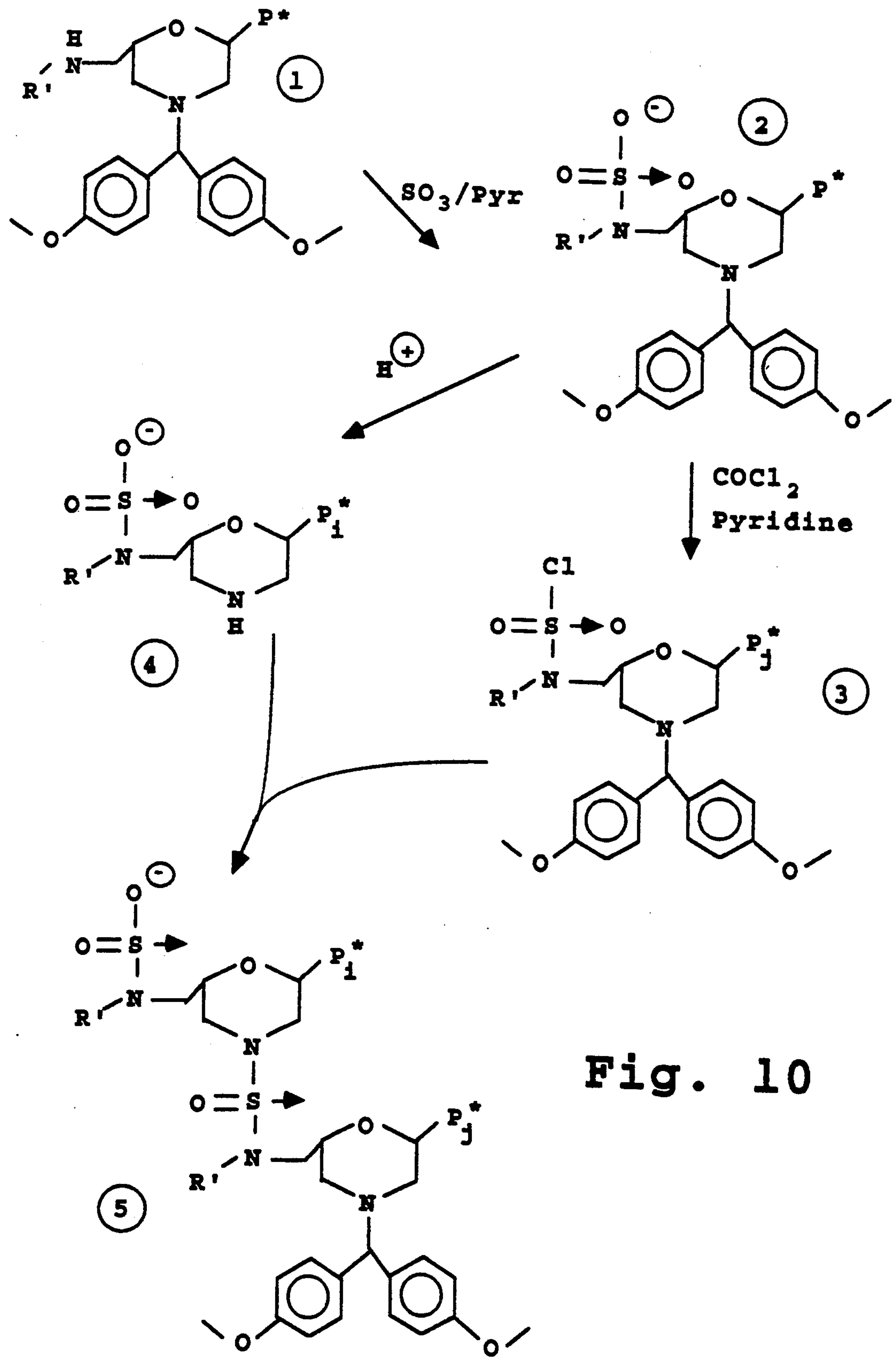
FIG. 10 shows the steps in linking two subunits through a sulfamide linkage (C—C)

The sulfamide linkage (corresponding to the linkage in structure C—C in FIG. 4, where X is a nitrogen), is formed by first sulfating the 5'-linked amine in a subunit, having a protected morpholino ring nitrogen, and then activating with phosgene. This subunit is then reacted with a second subunit having an unprotected ring nitrogen, as illustrated in FIG. 10. Details of the coupling reaction are given in Example 7.

The sulfamate linkage (corresponding to the linkage in Structure C—C in FIG. 4, where X is O) is produced by first sulfating the morpholino ring nitrogen of a 5' protected subunit, and then generating the sulfamoyl chloride derivative using phosgene. This activated subunit is then mixed with another subunit, or oligomer, having a free 5'OH. Coupling of the subunits is achieved either with a catalyst, such as silver trifluoromethanesulfonate, or use of a strong base to convert the 5' hydroxyl to the anionic form. Conversion of the 5' hydroxyl to the alkoxy can be achieved by KOH and a suitable phase transfer catalyst (e.g. 18-Crown-6).

Figure 11A:
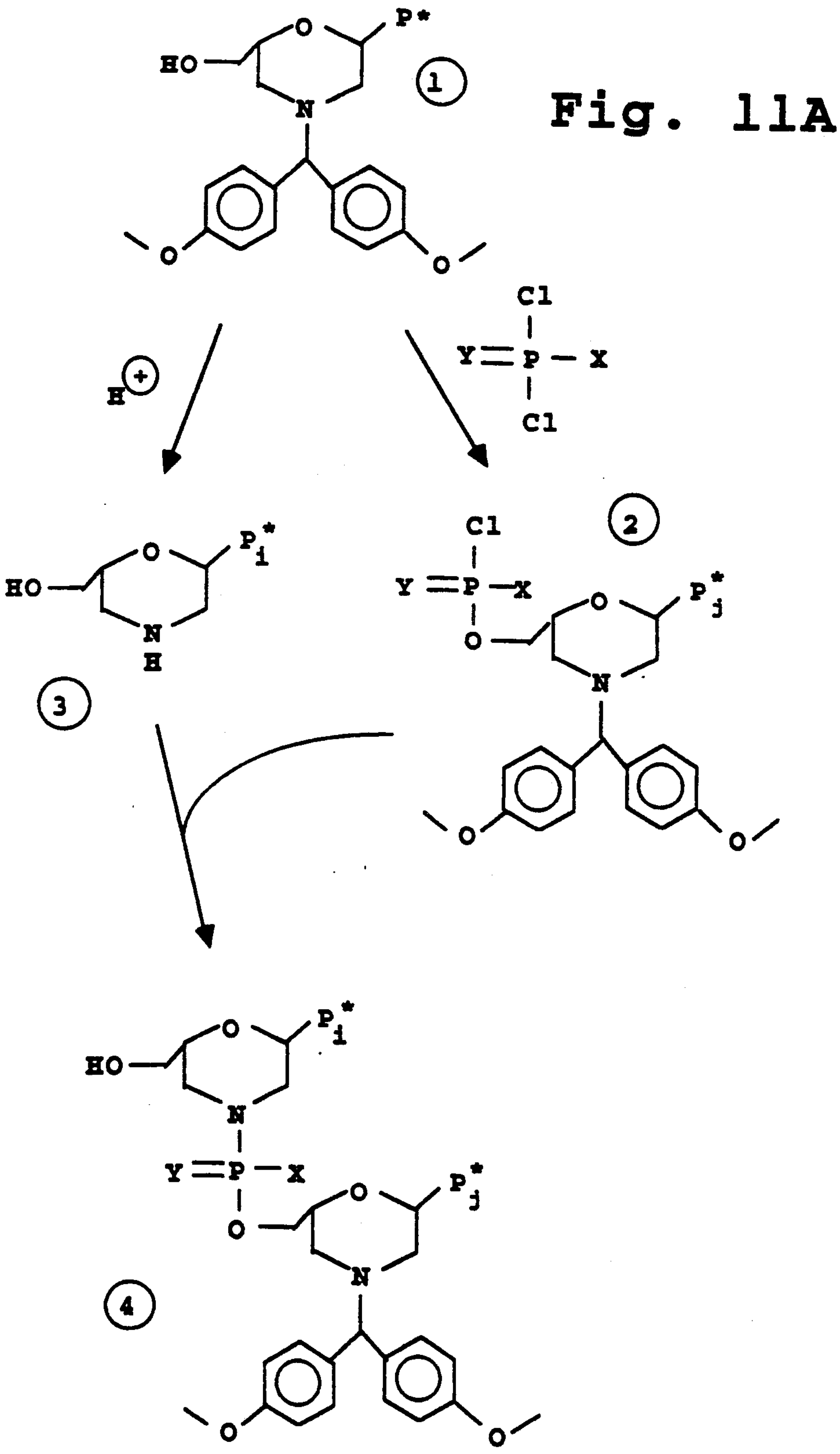
FIGS. 11A and 11B show the steps in linking two subunits through a phosphoramidate linkage (D—D)
Figure 11B:
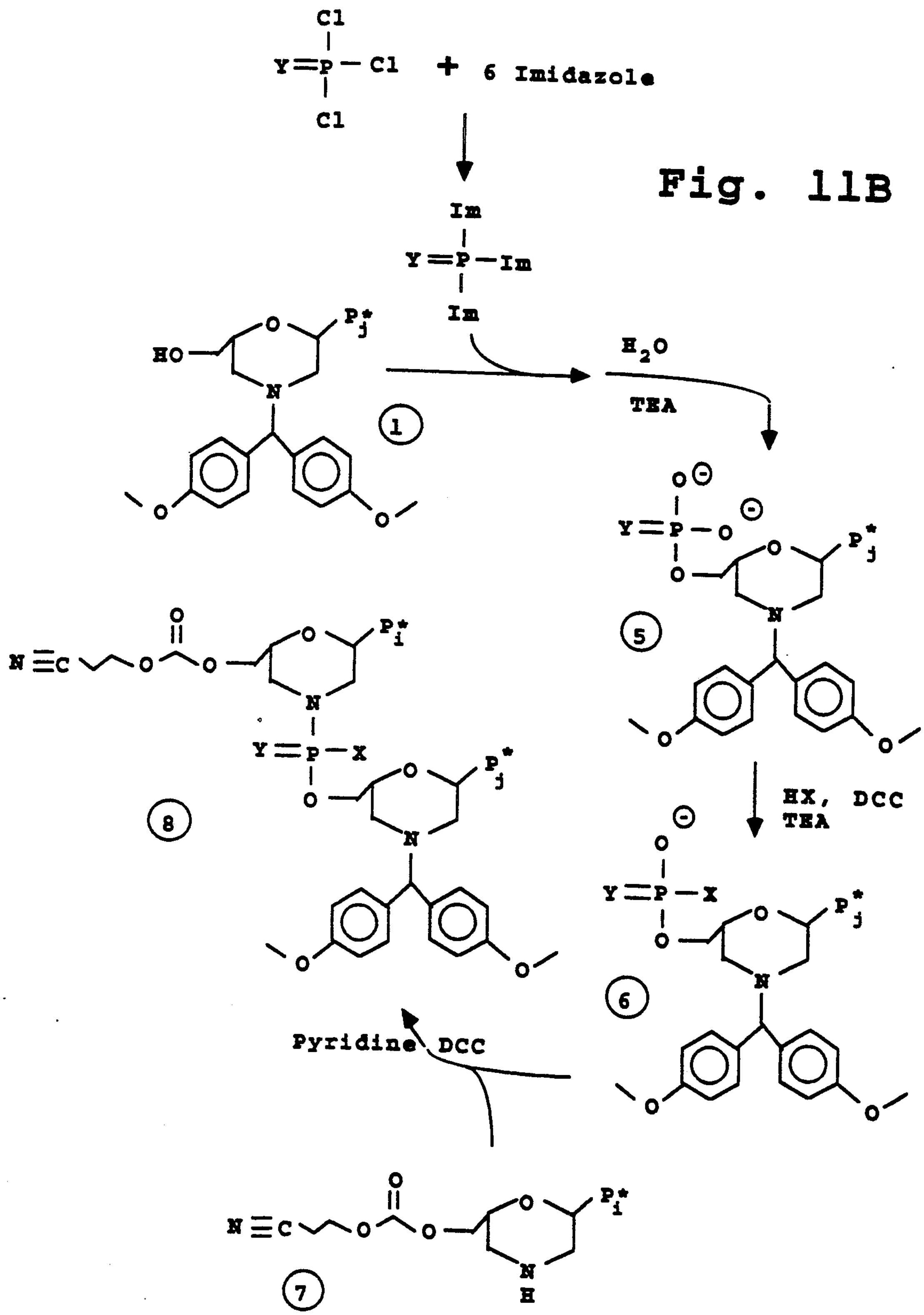

The phosphoramide linkage in Structure D—D of FIG. 4 (6-atom unit-length backbone) can be formed according to the reaction schemes shown in FIG. 11 and detailed in Example 8. The 5'hydroxyl of a protected subunit (Structure 1 of FIG. 11) is reacted with a suitable phosphorous-containing compound, such as dichloro-n,n-dimethylamine phosphate. The resultant activated subunit is then reacted with a second subunit having an unprotected morpholino ring nitrogen. A large number of variations are possible in the pendant X moiety and, as described in Example 8, the identity of the X moiety affects the ease of activation and coupling, the stability of the resultant linkage, and, to some extent, target-binding affinity.

In the syntheses of the D—D and G—G linkages the P+O group is essentially interchangeable with the P+S group; the methods of synthesis are generally the same.

An alternative method for forming linkages of type D—D of FIG. 4, as well as phosphoramidate and phosphonamidate linkages, is to use carbodiimide coupling. The carbodiimide couplings described in Examples 8 and 11 use dicyclohexyl carbodiimide (DCC). By exploiting an observation of Smith, et al. (1958) the carbodiimide reagent can also be used to: (a) add a phosphorous linking moiety to a subunit; or (b) attach a pendant X moiety to a phosphorous (or thiophosphorous) linking moiety.

A number of 7-atom unit length backbones, prepared from morpholino-subunits (structures E—E through G—G, FIG. 4), allow even more flexibility in the construction of polymers having specified distances between the base-pairing moieties. Using the 7-atom unit length linkages, distances between the morpholino-subunits, and consequently between the base pairing moieties, can be lengthened. Such lengthening of the intersubunit linkage is particularly useful when targeting duplex genetic sequences in a B conformation.

Figure 12:
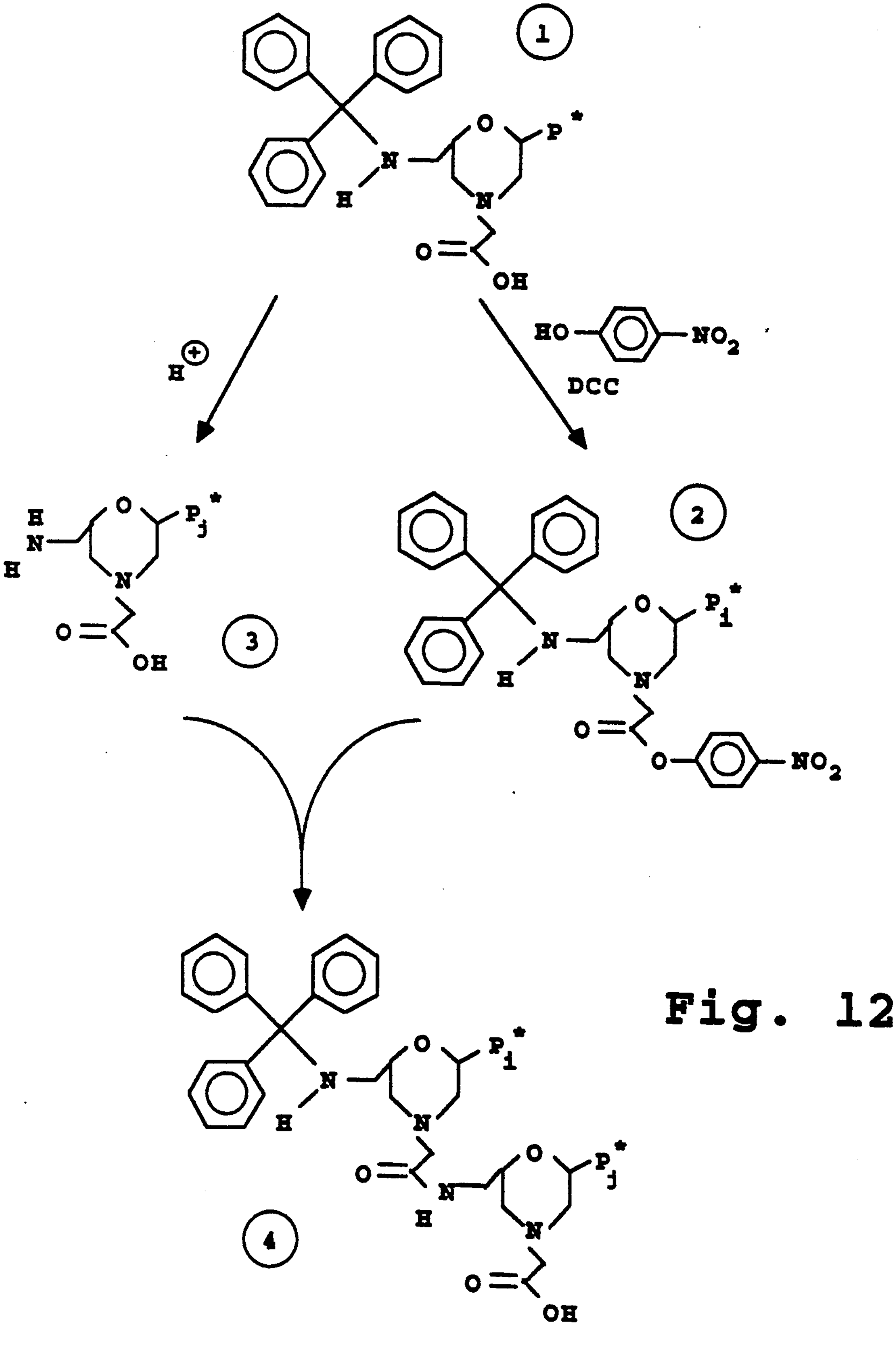
FIG. 12 shows the steps in linking two subunits through an amide linkage (E—E)
Figure 13:
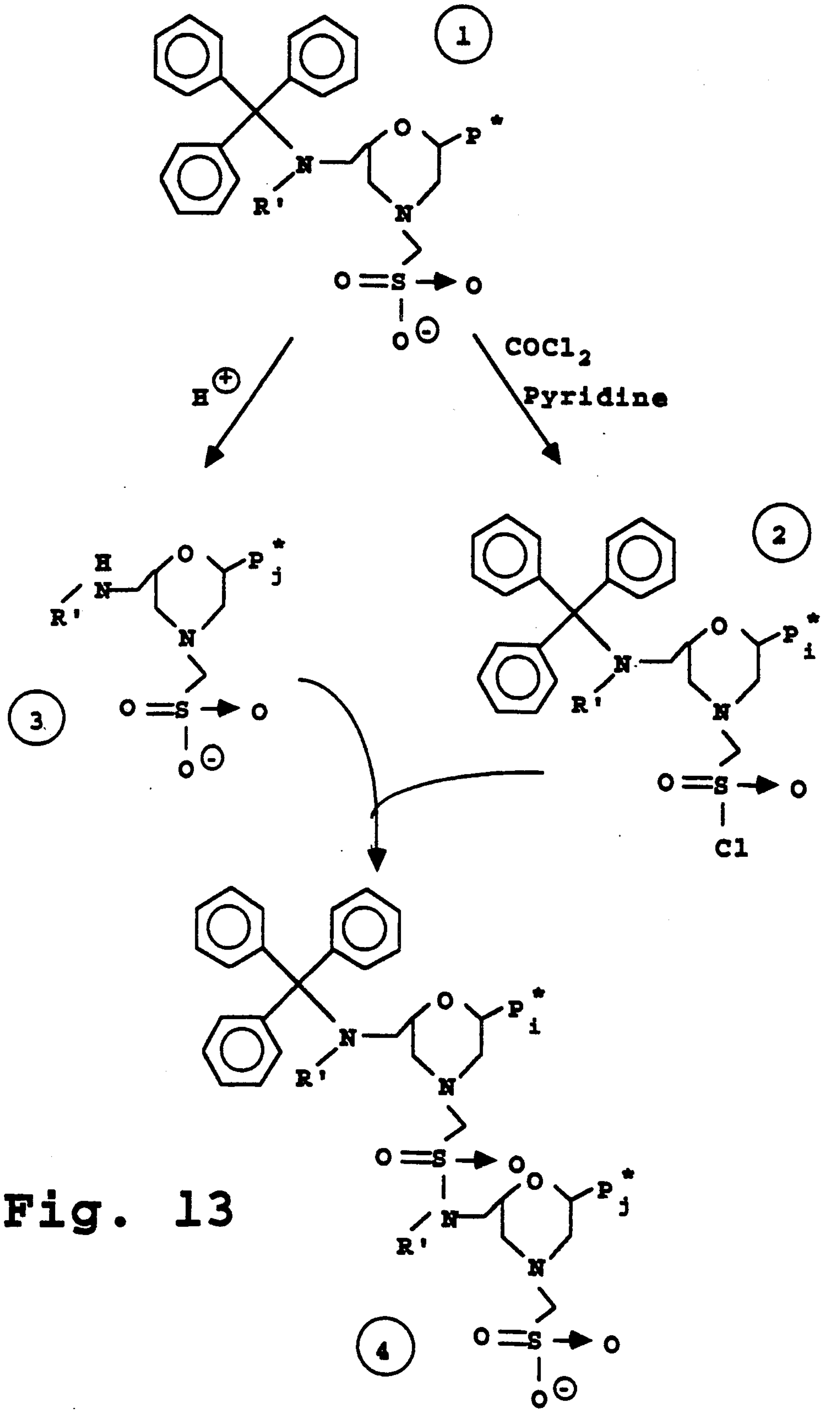
FIG. 13 shows the steps in linking two subunits through a sulfonamide linkage (F—F)

Structure E—E in FIG. 4 can be produced by activating the carboxyl group of a morpholino subunit with carbonyldiimidazole or a carbodiimide and reacting the activated subunit with a second subunit having an unprotected 5'-linked primary amine (FIG. 12, Example 9). Structure F—F in FIG. 4 can be produced by (a) reacting the sulfonyl group of the subunit D (Structure 1 of FIG. 13) with phosgene, and (b) coupling the activated subunit with a second subunit having an unprotected morpholino ring nitrogen (Example 10).

Figure 14:
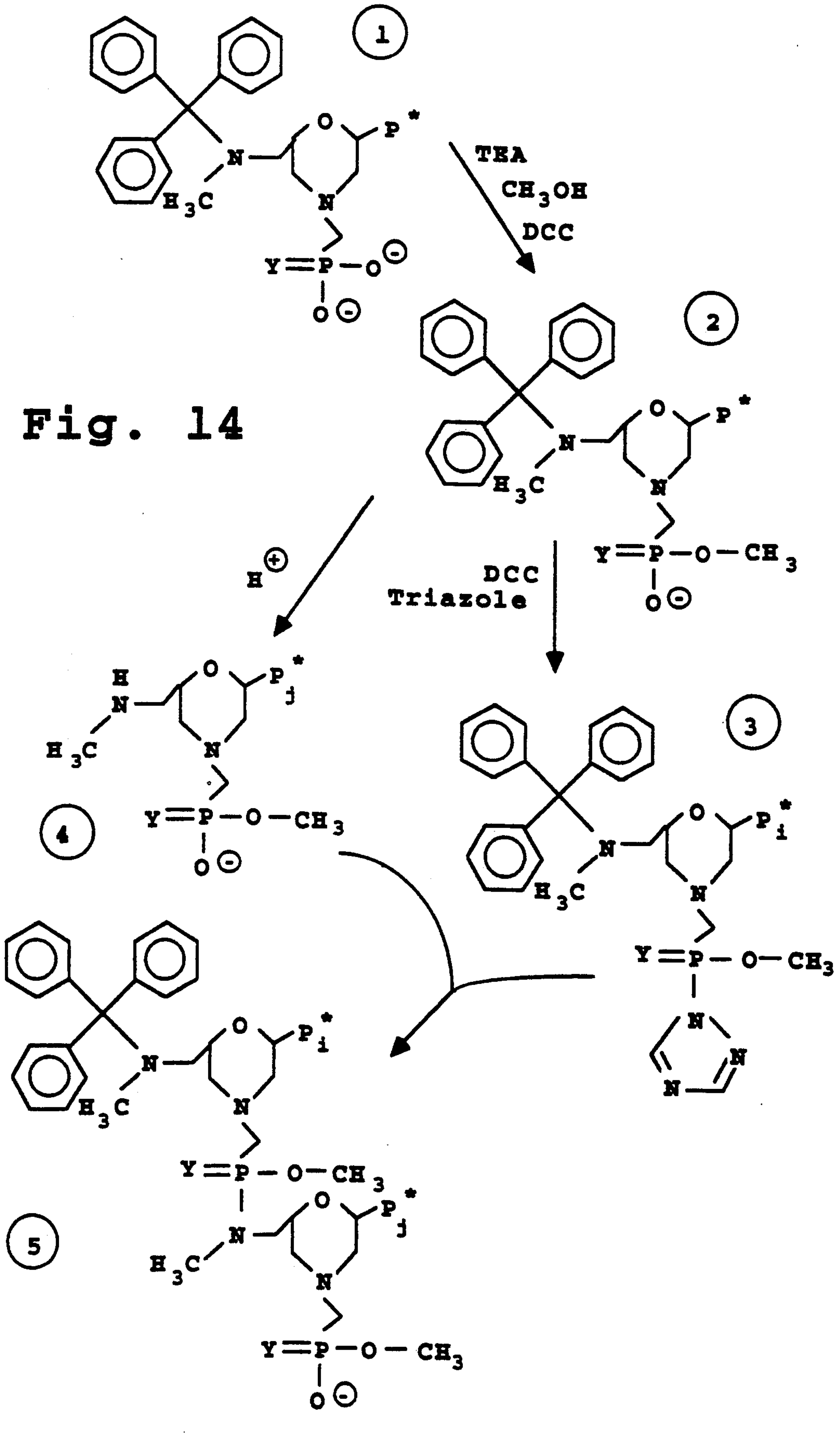
FIG. 14 shows the steps in linking two subunits through phosphonamidate linkage (G—G)

Similarly, Structure G—G in FIG. 4 can be produced by activating the phosphorous-containing group with a carbodiimide, and coupling the activated subunit with a second subunit having an unprotected 5'-linked amine, as illustrated in FIG. 14 and described in Example 11.

D. Assembly of Polymers

After selecting a desired polymer length and recognition moiety sequence (guidelines for this are presented below), the polymer is assembled using the general procedures described above. One method of polymer assembly involves initial preparation of an appropriate set of dimers, linking selected dimers to form tetrameres, linking these to form octamers, and so on. This method is carried out in solution, substantially according to the coupling methods described with reference to Examples 5-11. Example 12 outlines such a block assembly synthesis using monomers to form dimers, and dimers to form tetrameres. The synthesis need not involve oligomers of equal size.

A particular merit of this block assembly method is that each coupling product is roughly twice the length of its precursors, so purification of the product of each coupling is simplified. Example 12 details the assembly of a 4-subunit polymer formed by this method.

The polymers may also be synthesized by stepwise subunit addition on a solid support. However, the optimal synthetic approach often uses a combination of the solution and solid support assembly methods where dimers, trimers, or tetrameres are synthesized by solution phase and subsequently assembled into the full-length polymer on a solid support, as described in Example 13.

Typically, a solid support, such as glass beads derivatized with acid-stable, long-chain cleavable linkers, are employed as the support material, and prepared for attachment of the first subunit, or block of subunits, as described in Example 13. The glass beads are reacted with a subunit which generally has a readily cleavable protective group on a nitrogen. Whether the morpholino subunit is linked to the support via its morpholino nitrogen or a group at the 5' position depends on the direction of polymer synthesis, i.e., to which group the next subunit will be attached.

After coupling the second subunit (or oligomer which may be assembled in solution) to the support, any unreacted nucleophilic sites can be capped by addition of a suitable capping reagent, such as p-nitrophenyl acetate or acetic anhydride, and thereafter the support is washed. The protecting group on the nitrogen of the terminal subunit is removed, typically by acid treatment, and after neutralization, the support is reacted with an excess of the next-insequence subunit (or polymer unit) which is activated by one of the methods outlined above. One feature of the solid support assembly method is the need for high coupling efficiencies at each subunit addition step. This high coupling efficiency is generally achieved by addition of an excess of the activated subunit which maximizes the number of support-bound chains which are chain-elongated.

Chain elongation is continued in this manner, with optional capping of failure sequences after each subunit addition, until the polymer of the desired length and sequence is achieved.

After addition of the final subunit, the terminal backbone moiety may be reacted with a suitable group, as described in Example 13. The polymer is then cleaved from the support, e.g., by treatment with either ammonium hydroxide or a non-nucleophilic base suitable for effecting β-elimination in the linker joining the polymer to the support. The bases are deprotected and the polymer is purified as described below and in Example 13.

E. Polymer Processing and Purification

Binding polymers assembled in solution (Example 12) are typically base-deprotected by suspending in DMSO or DMF and layering on the suspension an equal volume of concentrated ammonium hydroxide. The preparation is mixed with shaking and incubated at 30° C. for 16 hrs. Workup includes removing the ammonia under reduced pressure. If a protective group (generally trityl or a related acid-labile moiety) is present, this group is cleaved and the crude polymer preparation is suspended in the appropriate buffer for purification (Example 13).

Binding polymers assembled by a solid-phase method (Example 13) where they are linked to the support via an ester linkage can be cleaved from the support by suspending the dried support in DMSO, layering on an equal volume of concentrated $NH_4OH$, capping tightly, and slowly agitating for 16 hrs at 30° C. The solid support material is removed by filtration and the filtrate is treated as described above.

Alternatively, binding polymers linked to the support via a β-elimination-sensitive linker can be cleaved from the support using a strong non-nucleophilic base 1,8 diazabicyclo(5.4.0.)undec-7-ene (DBU) in DMF. Using this approach one can release the polymer with its bases still protected and thus the polymer is suitable for further modification and/or structural confirmation via fast atom bombardment mass spectroscopy.

Purification of the base-deprotected polymer is preferably carried out at pH 2.5 or pH 11, depending on the pKs of the base moieties in the polymer. At pH 2.5 cytosine, adenine, and 2-6-diaminopurine moieties carry a positive charge and guanine carries a partial positive charge. At pH 11 guanine, uracil and hypoxanthine carry a negative charge.

For polymers in which about 50% or more of the base-pairing moieties are ionized at pH 2.5, the purification can be carried out by cation exchange on a column of S-Sepharose fast-flow (Pharmacia) developed with a shallow NaCl gradient buffered at pH 2.5. The effluent is monitored at 254 nm and collected in a fraction collector. The full length polymer, which elutes after the shorter failure sequences, can be further purified and desalted on a column of chromatographic grade polypropylene (Polysciences Inc.), eluted with an aqueous gradient of acetonitrile adjusted to pH 2.5 with formic acid, with the eluant being monitored at 254 nm. The fractions containing the pure product are neutralized and dried under reduced pressure. Salts may be discarded by dissolving the polymer in trifluoroethanol, filtering, and evaporating the trifluoroethanol.

For polymers in which about 50% or more of the base-pairing moieties are ionized at pH 11, the purification may be performed on an anion exchange column of Q Sepharose fast-flow (Pharmacia) developed with an aqueous pH 11 gradient of NaCl. The full-length polymer, which elutes after shorter failure sequences, is further purified and desalted on a polypropylene column eluted with an aqueous pH 11 gradient of acetonitrile. Fractions containing the pure product are processed as above.

The purification methods described above should be carried out so that polymers containing adenine base-pairing moieties are not exposed to pH 11 for more than a few hours at room temperature, to avoid potential base lability problems. The details of the purification methods are outlined in Example 13.

In neutral, aqueous solution, longer morpholino polymers may have solubilities only in the sub-micromolar range. Therefore, it may be advantageous to enhance polymer solubility by addition of one or more hydrophilic moieties, e.g., polyethylene glycol. For most of the polymer types disclosed herein, this can be accomplished by cleaving the terminal backbone protective group from the completed polymer, and reacting the polymer, with the bases still in the protected state, with excess of carbonyldiimidazole-activated polyethylene glycol (PEG). Thereafter the binding polymer is treated with ammonium hydroxide to remove the base-protected groups, and the polymer is purified as above. The level of solubilization is easily adjusted through proper selection of the PEG material. Suitable PEG fractions having average molecular weights of 200, 400, 600, 1,000, 1,540, 3,400, 4,000, 6,000, 7,500, and 18,500 daltons are commercially available (e.g., Polysciences, Inc.) with PEG1000 often providing the best solubilization. The solubilizing moiety may be linked to the polymer through a cleavable linkage, if desired, to allow the polymer to be released from the solubilizing agent, e.g., by esterase or peptidase enzymes.

It will be appreciated that the polymer may be further derivatized or labeled according to known procedures. For example, the polymer may be radiolabeled by preparing the polymer subunits from radiolabeled ribonucleosides or by attaching a radiolabeled amino acid at one terminus. The polymer may be readily derivatized, e.g., employing modifications of the above subunit coupling reactions, with enzymes, chromophoric groups, or the like, where the polymer is to be used as a diagnostic probe. Further, the polymer may be derivatized with biomolecules which serve to target the polymers to specific tissues or cell types.

F. Structural Characterization

Fully-protected binding polymers of moderate size (10 to 20 subunits) often give a strong molecular ion in FAB (Fast Atom Bombardment) mass spectroscopy, providing a key confirmation of the polymer length.

Further, COSY-NMR (two-dimensional correlated spectroscopy) of the deprotected and purified polymer provides information on the ratio of the different base-pairing moieties in the polymer as well as quantitative information on the ratio of binding polymer to any solubilizing or other type moiety which may have been linked thereto.

Mobilities on ion exchange columns also provide information on the number of C+A base-pairing moieties in a polymer when purification is carried out at pH 2.5 and information on the number of G+U residues when the purification is run at pH 11. Structural verification is easiest when the polymers have been assembled from oligomer blocks, such as in Examples 12 and 13, since any failure sequences then differ more substantially from the full-length sequences.

The UV profiles of the polymers at pH 1, 7, and 13 can provide information about the relative nucleotide composition of the polymer.

Assessment of a morpholino-based polymer's affinity for its target sequence is carried out by examining the melting curve of the polymer/target duplex.

Further, comparisons can be made between the melting curve of a regular nucleic acid duplex (such as $p(dC)_6/p(dG)_6$) and the melting curve of a hybrid duplex containing a corresponding morpholino-based polymer (such as (morpholino-based $C)_6/p(dG)_6$).

G. Diagnostic Applications

The target-specific polymers of the invention can be used in a variety of diagnostic assays for detection of RNA or DNA having a given target sequence. In one general application, the polymers are labeled with a suitable radiolabel or other detectable reporter group. Target polynucleotide, typically a single stranded polynucleotide which is bound to a solid support, is mixed with the polymer under hybridization conditions, allowed to anneal, and then the sample is examined for the presence of polymer reporter group.

The diagnostic assay can be carried out according to standard procedures, with suitable adjustment of the hybridization conditions to allow polymer hybridization with the target region. In this regard, the polymer can be designed for hybridization with the target at a higher melting temperature than the complementary polynucleotide strand, since polymer binding does not entail backbone charge repulsion effects. Therefore, the polymer can bind to the target at a temperature above the normal polynucleotide melting temperature, an important advantage of the polymer over conventional oligonucleotide probes. This binding at elevated temperature minimizes the problem of competition for binding to the target between the probe and any corresponding single-strand oligonucleotide which may be present in the diagnostic mixture.

In a second general type of diagnostic application, the polymers are linked to a solid support, for capture of target RNA or DNA to the support. The solid support, e.g., polymeric microparticles, can be prepared by linking the polymers to the support according to the methods described above or by conventional derivatization procedures. Alternatively, where the polymers are synthesized on a solid support this support may also serve as the assay support.

According to an important feature of this assay system, the target polynucleotide molecules which are captured on the support by base-specific binding to the polymers can be detected on the basis of their backbone charge, since the support-bound polymers are themselves substantially uncharged. To this end, the assay system may also include polycationic reporter molecules which are designed to bind to the fully charged analyte backbone, but not the uncharged (or substantially uncharged) polymer backbone, under selected binding conditions.

In one embodiment the reporter molecules are composed of a polycationic moiety or tail designed to bind electrostatically to a fully charged polynucleotide, under conditions where the reporter does not bind to the less charged or uncharged binding polymer carried on the diagnostic reagent; one or more reporter groups may be attached to the tail, adapted to produce a signal by which the presence of the reporter can be detected. Methods for forming polycationic molecules and for attaching reporter molecules to cationic compounds are known in the art.

Each reporter molecule carries one or more reporter groups, and each polynucleotide can accommodate binding of typically several thousand or more reporter molecules. Thus the system has an amplification factor, in terms of reporter signal per bound analyte molecule, of several orders of magnitude. In addition, the method has the advantage, described above, that the polynucleotide binding reaction can be carried out under conditions in which binding competition with complementary nucleotide strands does not occur.

The design considerations applied in preparing a polynucleotide binding polymer for use as a diagnostic reagent are governed by the nature of the target analyte and the reaction conditions under which the analyte is to be assayed. As a first consideration, there is selected a non-homopolymeric target base sequence against which the polymer is directed. This target sequence is generally single-stranded and preferably unique to the analyte being assayed.

The probability of occurrence of a given n-base target sequence is approximately $(\frac{1}{4})^n$. Accordingly, a given n-base target sequence would be expected to occur approximately once in a polymer containing $4^n$ bases. Therefore, the probability P that a given n-base sequence will occur in polynucleotides containing a total of N unique-sequence bases is approximately $P=N/4^n$. To illustrate, the probability P that a 9-base target sequence will be found in a 20 kilobase polynucleotide is about $20\times10^3/2\times10^5$ or 0.08, the probability that a 16-base target sequence will be present is about $20\times10^3/4.3\times10^9$ or 0.0000047. From these calculations, it can be seen that a polymer having 9-16 recognition moieties specific for a defined 9-16 base target sequence should have high specificity for the target sequence in an assay mixture containing only viral genomes, whose greatest complexities correspond to about 400K of unique-sequence bases.

Similar calculations show that a 12 to 16 subunit polymer can provide adequate specificity for a viral or bacterial target sequence in an assay mixture containing viral and bacterial genomic material only; largest genomic sizes about 5,000 kilobases. A 16 to 22 subunit polymer can provide adequate specificity for a target sequence in a polynucleotide mixture containing mammalian genomic DNA material; genomic sizes of about 5 billion base pairs of unique-sequence DNA.

The polymer/analyte binding affinity, and particularly the temperature at which the polymer just binds with the target sequence (the melting temperature, or Tm) can be selectively varied according to the following criteria: (a) number of subunits in the polymer; (b) the number of hydrogen bonds that can be formed between the base-pairing moieties and the corresponding, complementary bases of the analyte target sequence; (c) unit length of the polymer backbone; (d) the particular intersubunit linkages; and (e) concentration of denaturants, such as formamide, which reduces the temperature of melting.

From a number of studies on model nucleic acid duplexes it is known that the melting temperature of oligonucleotide duplexes in the 10 to 20 bp range increases roughly 3° C. per additional base pair formed by two hydrogen bonds, and about 6° C. per additional base pair formed by three hydrogen bonds. Therefore, the target sequence length originally selected to insure high binding specificity with the polymer may be extended to achieve a desired melting temperature under selected assay conditions.

Also, where the recognition moieties used in constructing the polymer are the standard nucleic acid bases the target sequence may be selected to have a high percentage of guanine plus cytosine bases to achieve a relatively high polymer/analyte melting temperature. On the other hand to achieve a lower melting temperature a target sequence is selected which contains a relatively high percentage of adenine plus thymine bases.

Figure 15:
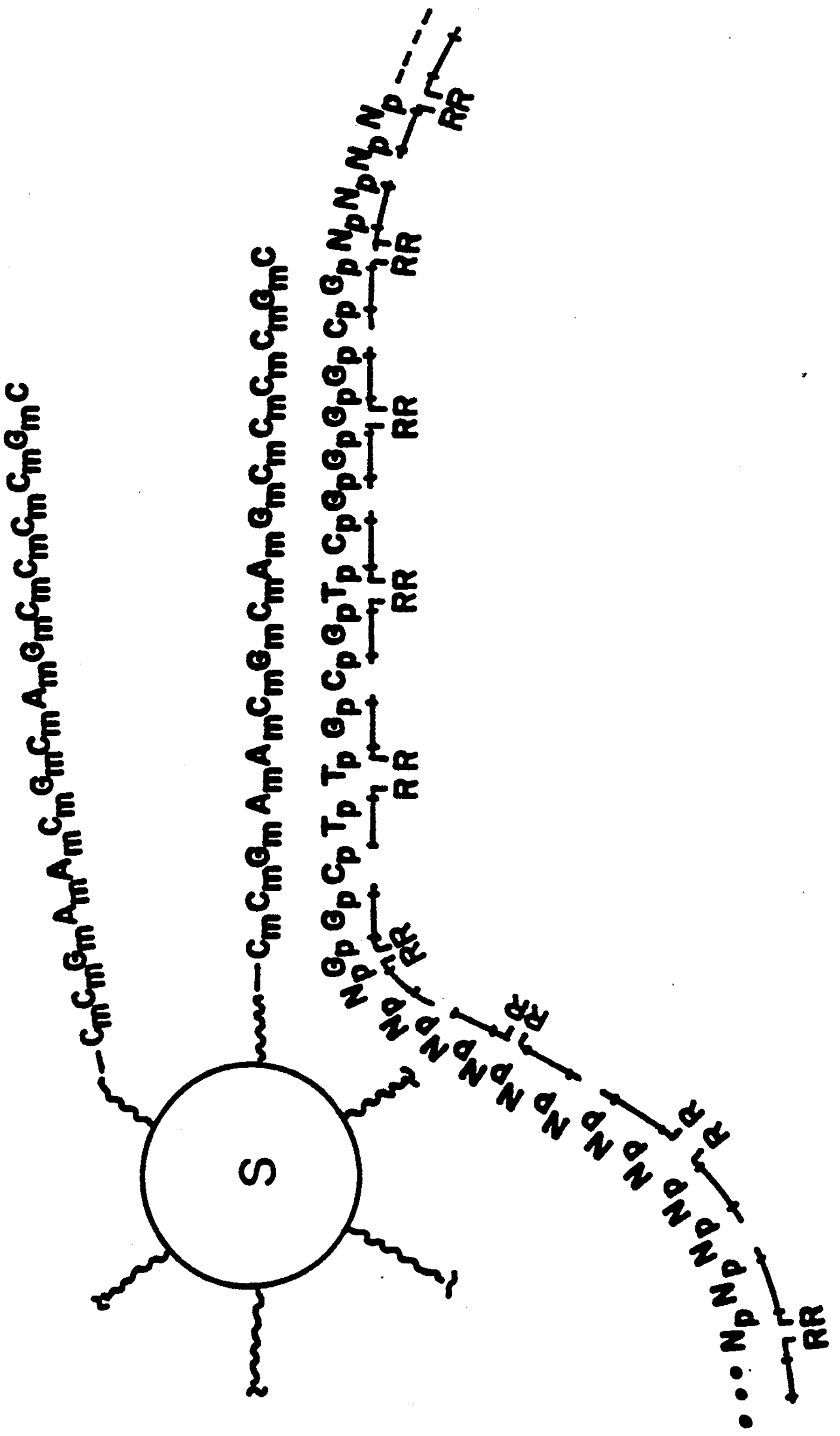
FIG. 15 illustrates the use of a morpholino polymer in a probe-diagnostic system.

The binding components in the diagnostic system, as they function in the solid-support diagnostic method just described, are illustrated in FIG. 15. Here "S", the assay reagent, is the solid support having a number of binding polymers attached to its surface through spacer arms indicated by sawtooth lines. In the assay procedure, the target DNA in single strand form is reacted with the support-bound polymers under hybridization conditions, and the solid support is then washed to remove non-hybridized nucleic acid material.

The washed support is then reacted with the reporter, under conditions which favor electrostatic binding of the reporter cationic moiety to the target DNA backbone. The reporter shown in FIG. 15 is a dicationic molecule having a reporter group R.

After reaction with the reporter solution, typically at room temperature for 1–2 minutes, the reagent is washed to remove unbound reporter, and then the assay reagent is assessed for bound reporter. One approach in determining the amount of reporter associated with the reagent, particularly in the case of fluorescent or chromophoric reporter groups, is to elute the reporter from the reagent with a high salt solution and then assess the eluate for reporter.

The polymer of the invention can undergo sequence-specific binding to duplex nucleic acids via base-pair-specific hydrogen bonding sites which are accessible through the major groove of the double helix. This bonding can occur in a duplex region in which at least 70% of the bases on one strand are purines and a corresponding percent of the bases on the other strand are pyrimidines. The duplex binding polymer preferably includes 2-aminopurine or 2,6-diaminopurine hydrogen bonding moieties for binding to T-A or U-A base pairs, and guanine or thioguanine hydrogen-bonding moieties for binding to C-G base pairs as illustrated in FIG. 8A. Thus, for these special target sequences (an example of which is shown in FIG. 8B), the polymer of the invention can be used for diagnostic assays of the types just described, but where the target nucleic acid is in non-denatured, duplex form.

H. Other Applications

The polymers of the instant invention can be used in place of standard RNA or DNA oligomers for a number of standard laboratory procedures. As mentioned above, morpholino-based polymers can be fixed to a solid support and used to isolate complementary nucleic acid sequences, for example, purification of a specific mRNA from a poly-A fraction (Goldberg et al). The instant polymers are advantageous for such applications since they are inexpensive and straightforward to prepare from activated subunits.

A large number of applications in molecular biology can be found for labeled morpholino-based polymers. Morpholino-based polymers can be easily and efficiently end-labelled by the inclusion in the last step of the polymer synthesis an activated and labelled morpholino-based subunit or, preferably, an $^{35}S$-labelled methionine. The type of label to be used is dependent on the final application of the polymer, and includes radioactive ($^{3}H$, $^{14}C$, $^{32}P$, or $^{35}S$) nucleosides and biotin. Labelled morpholino-based oligonucleotide analogs can act as efficient probes in, for example, colony hybridization (Grunstein et al), RNA hybridizations (Thomas), DNA hybridizations (Southern), and gene bank screening (Szostak et al).

The polymers of the invention also have important potential use as therapeutic agents. Recently, uncharged anti-sense nucleic acid analogs, which are nearly isostructural with DNA, have been used as anti-viral and anti-tumor agents. The polymers of the present invention provide several advantages over the more conventional anti-sense agents.

First, the morpholino polymers are substantially less expensive to synthesize than oligonucleotides. This is due in part to the fact that the morpholino subunits used in polymer synthesis are derived from ribonucleosides, rather than the much more expensive deoxyribonucleosides. Also, as described above, the coupling reaction between a phosphorous and an amine of a second subunit occurs under relatively mild conditions, so that protection steps and other precautions needed to avoid unwanted reactions are simplified. This is in contrast to standard ribo- and deoxyribonucleotide polymer synthesis where coupling through a phosphate ester linkage requires that the coupling reagents be highly reactive and that the reaction be carried out under stringent reaction/protection conditions. This advantage in polymer synthesis also applies, of course, to diagnostic uses of the polymer.

Second, polymer binding to its target may give substantially better target inactivation, since the polymer/target duplex is not susceptible to duplex unwinding mechanisms in the cell.

Third, the morpholino-based polymer is also more stable within the cell; the polymer backbone linkage is not susceptible to degradation by cellular nucleases.

Fourth, in therapeutic applications involving cellular uptake of the compound, the uncharged morpholino polymer is more likely to efficiently enter cells than a charged oligonucleotide.

In the context of therapeutic applications, the morpholino polymers of the present invention may be targeted against double-stranded genetic sequences in which one strand contains predominantly purines and the other strand contains predominantly pyrimidines (e.g., FIG. 8B).

Further, when a messenger RNA is coded by the mostly purine strand of the duplex target sequence, morpholino binding polymers targeted to the duplex have potential for also inactivating the mRNA. Thus such a polymer has the potential for inactivating key genetic sequences of a pathogen in both single-stranded and double-stranded forms.

In 1981 it was reported that short (3 to 7 subunits) methylphosphonate-linked DNA analogs complementary to portions of the Shine-Dalgarano consensus sequence of procaryotic mRNAs were effective in disrupting bacterial protein synthesis in bacterial lysates and in a special permeable strain of bacteria. However, such agents failed to inhibit protein synthesis in normal bacteria (Jayaramon, 1981).

Experiments performed in support of the instant invention show that polymers of 3 to 5 subunits in length can be effective to block protein synthesis in normal bacteria by using a combination of bases which result in a high target-binding affinity. More specifically, the following oligomers and oligomer combinations can perturb protein synthesis in normal intact bacteria (where D is 2,6-Diaminopurine or adenine; G is Guanine; B is 5-Bromouracil or other 5-Halouracil or Uracil; sequences are shown with their 5′ end to the left): DGG, BDDG, DDGG; DGGD; GGDG; GDGG; DGGB; GGBG; GGAGG; GGDGG; and the combinations BDD+GGDG; DDG+GDGG; DGG+DGGB; GGD+GGBG; BDDG+GDG; DDGG+DGG; DGGD+GGB; GGDG+GBG; BDD+GGDG+GBG.

While other backbone types may be suitable for such binding-enhanced short oligomers (e.g., carbamate-linked deoxyribonucleosides; Stirchak, 1987), the morpholino type oligomers of the present invention are preferred on the basis of starting material costs and ease of assembly.

The use of short binding-enhanced oligomers to disrupt the biological activity of an RNA sequence which plays a key role in the metabolism of a target class of organisms but not a correspondingly important role in higher organisms should be broadly adaptable to a variety of pathogenic organisms (e.g., bacteria and fungi) having a cell wall which excludes the entrance of longer polymers.

The following examples illustrate methods of subunit and polymer synthesis, and uses of the polymer composition of the invention. The examples are in no way intended to limit the scope of the invention.

EXAMPLE 1

Base Protection of Ribonucleosides

The following ribonucleosides are obtained from Sigma Chemical Co. (St. Louis, Mo.): uridine, guanosine, 5-methyluridine, adenosine, cytidine, 5-bromouridine, and inosine.

2,6-diamino-9-(B-D-ribofuranosyl)-9H-purine (2,6-diaminopurine riboside) is obtained from Pfaltz and Bauer, Inc., Division of Aceto Chemical Co., Inc. (Waterbury, Conn.).

The following nucleosides are prepared by the literature methods indicated:

1-β-D-ribofuranosyl)-2-pyrimidinone (2-hydroxy-pyrimidine riboside) is prepared by the procedure of Niedballa.

2-amino-9-β-D-ribofuranosyl)-1,6-dihydro-6H-purine-6-thione (thioguanosine) is prepared by the procedure of Fox.

Dimethoxytrityl chloride, N-6-benzoyladenosine, N-4-benzoylcytidine, and N-2-benzoylguanosine are obtained from Sigma Chemicals. 9-fluorenylmethoxycarbonyl chloride (FMOC chloride), trimethylchlorosilane, isobutyric anhydride, 4-nitrobenzoyl chloride, naphthalic anhydride, and all organic solvents for reactions and chromatography were obtained from Aldrich Chemical Co. (Milwaukee, Wis.). Silica Gel is obtained from EM Science (Cherry Hill, N.J.).

When activation of the subunits is achieved using dihalogenated electrophiles (e.g. $COCl_2$, $SO_2ClF$, $P(O)Cl_2N(CH_3)_2$ or $P(S)Cl_2(O-CH_2CH_3)$), better yields of activated subunits are often obtained by using protective groups which leave no acidic protons on the purine and pyrimidine exocyclic amines. Examples of such exocyclic amine moieties are as follows: the N6 of adenine, the N4 of cytosine, the N2 of guanine, and the N2 and N6 of diaminopurine. Suitable protective groups for this purpose include the naphthaloyl group (Dikshit) and the amidine groups developed by McBride et al (1986). In addition, use of dihalogenated electrophiles for subunit activation generally requires that the O6 of guanine moieties is protected; this protection is achieved using the diphenylcarboamoyl group (Trichtinger).

Guanosine

In order to minimize side reactions during subunit activations it is often desirable to protect the guanine moiety on both the N2 and O6 using the procedure of Trichtinger et al (1983). The N-2 9-fluorenylmethoxycarbonyl derivative of guanosine is prepared by the procedure below which is general for the protection of nucleoside amino groups: guanosine (1 mmol) is suspended in pyridine (5 ml) and treated with trimethylchlorosilane (5 mmol). After stirring for 5 minutes conc. ammonia (1 ml) is added, and the reaction is stirred for 15 minutes. The solution is evaporated to near dryness and the residue is dissolved in chloroform (10 ml). This solution is washed with sodium bicarbonate solution (5 ml, 10%), dried over sodium sulfate and evaporated. The residue is coevaporated several times with toluene and the product chromatographed on silica gel using a gradient of methanol in methylene chloride (0–50%).

N-2-Isobutyrylguanosine is prepared by the method of Letsinger. Further protection of the O6 is often desirable and can be carried out by several methods (Gait, 1984) with a nitrophenethyl moiety.

N-2-acetylguanosine is obtained by the method of Reese.

N-2-naphthaylguanosine is prepared by the method of Dikshit; this reference provides a general method for the protection of nucleoside amine groups.

Adenosine

The N-6 2-(4-nitrophenyl)-ethoxycarbonyl derivative is prepared by the method of Himmelsbach.

N-6 (4-nitrobenzoyl)adenosine is prepared using the procedure above for FMOC-guanosine except that 4-nitrobenzoyl chloride is substituted for FMOC chloride.

The N-6 2-(phenylsulfonyl)-ethoxycarbonyl derivative is prepared by the procedure for FMOC guanosine except the 2-(phenylsulfonyl)-ethyl chloroformate (Balgobin) is used as the acylating agent and N-methylimidazole or pyridine is used as the solvent.

N-6 naphthoyladenosine is prepared by the method of Dikshit; this reference provides a general method for the protection of nucleoside amine groups.

2,6-diaminopurineriboside

The N-2,N-6-bis(9-fluorenylmethoxycarbonyl) derivative of 2,6-diaminopurine riboside is prepared by the general procedure described for guanosine.

The N-2,N-6-bis(isobutyryl) derivative is prepared by the general procedure described for guanosine.

Thioguanosine

The N-2(9-fluorenylmethoxycarbonyl) derivative of thioguanosine is prepared by the general procedure described for guanosine.

Uridine

To minimize undesired side products during the subunit activation step it is sometimes desirable to protect the N3 of the uracil moiety. 5'O-tritylated uridine-2',3'-acetonide is converted to the N3 anisoyl derivative by the procedure of Kamimura et al (1983). The product is then treated with hot 80% acetic acid or 0.1N HCl in THF to cleave the protective groups on the ribose moiety.

EXAMPLE 2

Synthesis of Alpha Morpholino Ribonucleoside Derivative Having a Cleavable R Group This example describes the synthesis of α-morpholino subunits which have cleavable R-groups on the ring nitrogen. This example is described with reference to the structures shown in FIG. 5.

The base-protected ribonucleoside (Structure 1) is protected at the 2',3'hydroxyls with phenylboric acid by established methods (Ferrier, 1978).

The 5'hydroxyl of the protected ribonucleoside (Structure 2, FIG. 5) is converted to the 5' amine as follows. To 500 ml of DMSO is added 1.0 mole of pyridine (Pyr), 0.5 mole of trifluoroacetic acid (TFA), and 0.1 mole of the ribonucleoside. The mixture is stirred until dissolved, and then 0.5 mole of diisopropylcarbodiimide (DIC) or dicyclohexylcarbodiimide (DCC) is added to the mixture. After 2 hours the reaction mixture is added to 8 liters of rapidly stirred brine, stirred for 30 minutes, and then filtered. The solid obtained from the mixture is dried briefly (Structure 3A), washed with 1 liter of ice-cold hexanes, and filtered. The solid is added to 0.2 mole of sodium cyanoborohydride in 1 liter of methanol and the solution stirred for 10 minutes. 0.4 mole of benzotriazole or p-nitrophenol is then added to the solution, followed by the addition of 0.2 mole of 4,4'-dimethoxybenzhydralamine (Greenlee, 1984); the preparation is stirred four hours at room temperature [Note: the benzotriazole or p-nitrophenol buffers the reaction mixture to prevent racemization at the 4' carbon of the subunit at the iminium stage of the reductive alkylation]. Finally, the reaction mixture is poured into 5 liters of water, stirred until a good precipitate forms, and the solid is collected and dried (Structure 4, FIG. 5, where R is 4,4'-dimethoxybenzhydral).

Any remaining phenylboronate is removed with aqueous acetone or 1,3-propanediol. The product is oxidized in methanol using 1.1 equivalents of sodium periodate at room temperature for 90 minutes (Structure 5). This oxidation is followed by a reduction by adding 2 equivalents of sodium cyanoborohydride to the reaction mixture to give a morpholino derivative having a 5' aldehyde in the alpha orientation (Structure 6).

The above procedure generates a product where R is a 4,4'-dimethoxybenzhydryl moiety. During polymer assembly the moiety can be cleaved using a weak acid (1% formic acid or 2% acetic acid in trifluoroethanol). On the other hand, instead of reacting the initial 5' beta-aldehyde with the acid-cleavable 4,4'-dimethoxybenzhydryl amine, the aldehyde can be reacted with benzylamine or, preferably, with p-nitrobenzylamine. The resulting R group can then be cleaved by catalytic hydrogenation. Further, the initial 5'-betaaldehyde can instead be treated with ammonia to yield a product where R is a hydrogen. In this case the subsequent morpholino ring nitrogen is most commonly protected with trityl chloride which can be cleaved during polymer assembly using 1% formic acid or 2% acetic acid in trifluoroethanol; protection with trityl chloride is described below.

One-tenth of a mole of the above product (Structure 6 where R is hydrogen) is added with stirring to 2 liters of acetonitrile, followed by the addition of 0.26 mole of triethylamine and 0.15 mole of trityl chloride. The mixture is covered and stirred for 1 hour at room temperature. One hundred milliliters of methanol is added to the mixture and the stirring continued for 15 minutes. The preparation is dried under vacuum and suspended as a slurry in 5 liters of water and filtered. The solid is again washed with 1 liter of water, filtered, and dried under vacuum. The solid is resuspended in 500 ml of dichloromethane, filtered, and the filtrate rotovaped until precipitation just begins. As the precipitate begins to form, 1 liter of hexane is added to the solution and stirred for 15 minutes. The solid is removed by filtering and dried under vacuum. This procedure yields the base-protected morpholino derivative tritylated on the morpholino nitrogen and having a 5' aldehyde in the alpha orientation.

In the synthesis where R is hydrogen (Structure 6 of FIG. 5), there can be significant losses due to reaction between the ring nitrogen of one molecule and the 5' aldehyde of another while NaCNBH$_3$ is present. Accordingly, yields of product are generally better when the R group is a substituted alkyl.

EXAMPLE 3

Synthesis of Alpha-Morpholino Ribonucleoside Derivative Having a Linkable R Moiety This example describes the synthesis of α-morpholino subunits which have linkable R moieties. This example is described with reference to FIG. 5.

The base-protected ribonucleoside (Structure 1) is protected at the 2', 3'-hydroxyls using phenylboric acid and oxidized at the 5'-OH (Example 2). One-tenth mole of the resultant 5'-beta-aldehyde (Structure 3a) is added to 0.2 mole of sodium cyanoborohydride in 1 liter of methanol. To this solution 0.2 mole of aminomethanesulfonic acid, 0.2 mole of benzotriazole, and 0.2 mole of triethylamine are added and the preparation is stirred for four hours at room temperature, after which 100 ml of water is added to cleave the phenylboronate group from the 2' and 3' oxygens of the ribose moiety. The resulting product is purified by silica gel chromatography using a chloroform/methanol mixture 1% in triethylamine, to give Structure 4, where R is the triethylammonium salt of methanesulfonic acid. The product is suspended in methanol and 1.1 equivalent of sodium periodate is added to the solution, followed by the addition of 2 equivalents of sodium cyanoborohydride. After 1 hour the product is chromatographed, as above, to give Structure 6 where R is as above.

Related products can be prepared using glycine or aminomethanephosphonic acid instead of the above aminomethanesulfonic acid.

EXAMPLE 4

Conversion of 5'-alpha-aldehyde to Linkable Moieties

This example describes the conversion of the 5'-aldehyde to a number of functional groups. The steps in the method are described with reference to structures shown in FIG. 6.

a) Conversion to Amine

One-tenth mole of $\alpha$-morpholino subunit from Example 2 or 3 (Structure 6 of FIG. 5) is added to a mixture of 0.2 mole of sodium cyanoborohydride in 1 liter of methanol. Two-tenths mole of ammonia (R'=H), or a primary amine (R'=alkyl), and 0.4 mole of benzotriazole are then added to the mixture. The preparation is stirred 4 hours at room temperature resulting in the product shown as Structure 2. When R is a linkable group, such as prepared in Example 3, the new 5'-alpha amine moiety is generally protected using trityl chloride (Structure 2a).

b) Conversion to Hydroxyl

One-tenth mole of $\alpha$-morpholino subunit from Example 2 or 3 (Structure 6 of FIG. 5) is added to a mixture of 0.2 mole of sodium borohydride in 1 liter of isopropanol. The resulting mixture is stirred for 1 hour resulting in the product shown as Structure 3.

c) Conversion to Sulfhydral

One-tenth mole of the 5'-hydroxyl subunit (Structure 3, prepared as above) is added to 1 liter of pyridine. To this solution 0.12 mole of toluenesulfonyl chloride is added and the mixture stirred for 3 hours at room temperature. The pyridine is removed by rotovaping, followed by the addition of 0.5 mole of fresh sodium hydrosulfide in 1 liter of methanol. This mixture is stirred at room temperature overnight. The reaction mix is added to 5 liters of water, stirred for 20 minutes, and the solid collected giving the product shown as Structure 5.

d) Conversion to Sulfonate

One-tenth mole of Structure 5' where R is a benzhydraloxy carbonyl group (prepared as above), is dissolved in acetone or a t-butanol/water mixture; two-tenths mole magnesium sulfate and 0.5 mole potassium permanganate are added. The mixture is stirred at room temperature until the reaction is complete. The mixture is then filtered and treated with excess aqueous $NaHSO_3$ to decompose $KMnO_4$ and $MnO_2$. The filtrate is partitioned between water containing 2% triethylamine hydrochloride and chloroform. The chloroform layer is dried down; silica gel chromatography of the resulting solid yields the purified product (Structure 6).

EXAMPLE 5

Activation and Coupling to Give Sulfonamide Intersubunit Linkage (A—A)

.This example describes the activation and coupling of sulfonic acid subunits which were prepared in Example 4d. This example is described with reference to structures in FIG. 7.

Activation

Ten mmole of the triethylamine salt of sulfated subunit, protected on the base and on the nitrogen of the morpholino ring (Structure 1 of FIG. 7), is dissolved in 10 ml of dichloromethane. To this solution 40 mmole of pyridine is added. This solution is chilled for 15 minutes on a bed of dry ice and then 1.1 mmole of phosgene (20% in Toluene) is slowly added while the solution is rapidly stirred. The solution is then allowed to come to room temperature, is washed with aqueous $NaHCO_3$, and dried. The resulting solid is chromatographed on silica gel eluted with a mixture of chloroform and acetone yielding the desired sulfonyl chloride (Structure 2).

Deprotection

Eleven mmole of the triethylamine salt of sulfonate subunit (Structure 1 of FIG. 7) is dissolved in 200 ml of dichloromethane. To this solution 0.1 ml of dichloroacetic acid is added. After 5 minutes the solution is concentrated under reduced pressure and the deprotected subunit (Structure 3 of FIG. 7) precipitated with ether. The precipitate is washed thoroughly with ether and then resuspended in 5 ml of DMF containing 0.6 ml of triethylamine.

Coupling

The activated subunit (Structure 2) is added to the DMF solution already containing the deprotected subunit (Structure 3). This mixture is incubated at room temperature for 1 hour to give coupled product (Structure 4).

EXAMPLE 6

Activation and Coupling To Give Carbamate Linkage

This example describes the activation of 5'hydroxyl morpholino subunits, as prepared in Example 4b, and their subsequent coupling via a carbamate linkage to yield a 6-atom unit-length backbone. The example is described with reference to the structures in FIG. 9.

Activation Step

One millimole of dry, N-protected, 5'hydroxyl morpholino subunit (Structure 1), prepared as in Example 4b, is treated with 1.5 mmole of bis-(p-nitrophenyl)carbonate (BNPC) and 3 mmole of triethylamine (TEA) in 10 ml of DMF under anhydrous conditions. The solution is stirred for three hours and then evaporated to dryness. The resulting residue is dissolved in chloroform and chromatographed on silica gel eluted with chloroform/5% methanol/0.1% TEA, giving the activated subunit shown as Structure 2.

Deprotection Step 1.1 mmole of a morpholino subunit (Structure 1) is dissolved in 10 ml trifluoroethanol and 0.1 ml formic acid is added. After five minutes the trifluoroethanol and formic acid are evaporated under reduced pressure. The deprotected subunit (Structure 3) is resuspended in 5 ml DMF containing 0.5 ml triethylamine.

Coupling

The activated subunit produced above (Structure 2) is added to the DMF solution containing the unprotected subunit (Structure 3). The mixture is incubated at room temperature for 1 hour and results in the coupled product shown as Structure 4.

EXAMPLE 7

Sulfation, Activation and Coupling to Form Sulfamide Intersubunit Linkage

This example describes the sulfation of 5'-alpha amine subunits, prepared as in Example 4a, and the activation and coupling of these subunits via a sulfamide intersubunit linkage. This example is described with reference to structures in FIG. 10.

Sulfation

The 5'-amine subunit is prepared as in Example 4a (Structure 1). Twenty mmole of this subunit is suspended in 200 ml of DMF. To this solution 80 mmole of $SO_3$/pyridine complex is added. One hundred sixty mmole of triethylamine is added dropwise with stirring over a period of several hours. After the addition of the triethylamine is complete the solution is stirred for an additional two hours and then the preparation is dumped into two liters of brine. The resulting solid is collected by filtration and dried, giving the triethylammonium salt of structure 2.

Activation

Ten mmole of the triethylamine salt of sulfated subunit, base-protected and protected on the nitrogen of the morpholino ring (Structure 2 of FIG. 10), is dissolved in 10 ml of dichloromethane. To this solution 40 mmole of pyridine is added. The solution is chilled for 15 minutes on a bed of dry ice and then 1.1. mmole of phosgene (20% in Toluene) is slowly added while the solution is rapidly stirred. The solution is then allowed to come to room temperature, washed with aqueous $NaHCO_3$, and dried. The resulting solid is dissolved in dichloromethane and purified by chromatography using silica gel eluted with a mixture of chloroform-/acetone, 4:1 v/v, resulting in the sulfamoyl chloride shown as Structure 3 (FIG. 10).

Deprotection

Eleven mmole of the triethylamine salt of sulfated subunit (Structure 2, FIG. 10) is dissolved in 10 ml of trifluoroethanol followed by the addition of 0.1 ml of formic acid. After 5 minutes the solution is concentrated under reduced pressure and the deprotected subunit (Structure 4, FIG. 10) is precipitated with ether. The precipitate is washed thoroughly with ether and resuspended in 5 ml of DMF containing 0.6 ml of triethylamine.

Coupling

The activated subunit (5 mmole) (Structure 3) is added to the DMF solution containing 5.5 mmole of the deprotected subunit (Structure 4) and the mixture incubated at room temperature for 1 hour. This reaction results in the coupled product shown as Structure 5.

EXAMPLE 8

Activation and Coupling to Give Phosphoramide Linkages

A. X=—$CH_3$

Example 8A describes the coupling of a 5'hydroxyl subunit, prepared as in Example 4b, to a second subunit having a free morpholino ring nitrogen to give an alkylphosphonamidate intersubunit linkage. This example is described with reference to structures in FIG. 11A, where X is an alkyl group.

One mmole of 5'hydroxyl subunit, base-protected and protected on the morpholino nitrogen (Structure 1), is dissolved in 20 ml of dichloromethane. To this solution 4 mmole of N-ethylmorpholine and 1.1 mmole of methylphosphonic dichloride, for Y=O, are added, followed by the addition of 1 mmole of N-methylimidazole. After one hour the reaction solution is washed with aqueous $NaH_2PO_4$. This solution is then fractionated on a silica gel column developed with ethyl acetate to purify the activated subunit (Structure 2 in FIG. 11, where X is methyl). This activated subunit is added to 10 ml of DMF containing 1 mmole of a second subunit having an unprotected morpholino nitrogen (Structure 3) resulting in the dimer shown as Structure 4 (where X is —$CH_3$).

The alkylphosphonamidate intersubunit linkage is very stable to ammonia used for base deprotections; in contrast, the linkage is sensitive to fairly strong acids. For instance, the linkage has a half time of cleavage of about 3 hours in 2% dichloroacetic acid in dichloromethane. However, the linkage shows no detectable cleavage after 18 hours in 2% acetic acid in trifluoroethanol; conditions suitable for deprotection of the morpholino nitrogen.

B. X=—O—$CH_2CH_3$

Example 8B describes the coupling of a 5'hydroxyl subunit, prepared as in Example 4b, to a second subunit, having a free morpholino ring nitrogen, resulting in a phosphodiesteramide intersubunit linkage. This example is described with reference to structures in FIG. 11, where X is an alkoxide group.

One mmole of 5'-hydroxyl subunit, base-protected and protected on the morpholino nitrogen (Structure 1 of FIG. 11), is suspended in 80 ml of benzene. To this suspension 2.2 mmole of N-methylimidazole is added and the solution is stirred at room temperature until the subunit is dissolved. 1.2 mmole of ethyl dichlorophosphate for Y=O (or ethyldichlorothiophosphate for Y=S) is added to the solution. After one hour the reaction solution is washed with aqueous $NaH_2PO_4$. The solution is then loaded on a silica gel column and developed with ethyl acetate to obtain the activated subunit shown as Structure 2 in FIG. 11 (where X is —O—$CH_2CH_3$). As in Example 8A, the activated subunit can be added to a DMF solution containing a second subunit, having a free morpholino nitrogen (Structure 3), to give the dimer shown as Structure 4.

When ethyldichlorothiophosphate (Y=S) is used for activation of the subunits, improved yields are obtained with the following modifications. One mmole of 5' hydroxyl subunit, base-protected and tritylated on the morpholino nitrogen (structure 4 of FIG. 5), is suspended in 20 ml of chloroform. To this solution 1 ml of N-methylimidazole is added, followed by the addition of 1.6 ml of ethyldichlorothiophosphate (Aldrich Chem. Co.). After 1 hour the subunit product is purified by silica gel chromatography developed with 20% acetone/80% chloroform. This activated subunit (Structure 2, where X is —O—$CH_2$—$CH_3$ and Y is sulfur) can be coupled to the morpholino nitrogen of a second subunit as described above.

An alternative synthesis of a phosphodiesteramide intersubunit linkage involves the use of a carbodiimide. One mole of imidazole is dissolved in DMF and the DMF removed under vacuum. The dry imidazole is then dissolved in dichloromethane, followed by the slow addition, with stirring, of 0.15 mole of phosphorous oxychloride ($P(O)Cl_3$). Ten minutes after the addition of $P(O)Cl_3$ is complete, 0.1 mole of 5'hydroxy subunit, prepared as in Example 4b, is added and the solution stirred for one hour. Four-tenths mole of triethylamine and one mole of water is added and the solution stirred for 30 minutes. The dichloromethane is then removed under reduced pressure to give Structure 5. The solid is triturated with water, dissolved in ethanol, rotovaped dry, and resuspended in ethanol containing 0.25 mole of triethylamine. Two-tenths mole of dicyclohexylcarbodiimide (DDC) is then added and the resulting solution stirred two hours at room temperature. This reaction yields structure 6, where X is an ethoxy moiety. The product (Structure 6) is dissolved in chloroform and shaken with an aqueous solution 2% in pyridine hydrochloride. The chloroform layer is dried down yielding the pyridinium salt of structure 6. This salt is suitable for carbodiimide coupling to second subunit, having a protected 5' moiety and a free morpholino ring nitrogen (e.g., structure 7), to give the desired phosphodiesteramide linkage (structure 8).

For carbodiimide coupling, the presence of a relatively strong base (e.g., triethylamine) allows the reaction of only one X moiety of the phosphorylated subunit (structure 5) in the presence of a carbodiimide (giving structure 6). In order to react a second group with that phosphate, as in the case of dimer formation shown as Structure 8, the counter ion to the phosphate must be a relatively weak base, such as pyridine.

C. X=—$N(CH_3)_2$

Example 8C describes the coupling of a 5'hydroxyl subunit, prepared as in Example 4b, to a second subunit, having a free morpholino ring nitrogen, to give a phosphordiamidate intersubunit linkage. This example is described with reference to structures in FIG. 11, where X is a disubstituted nitrogen.

One mmole of 5'hydroxyl subunit, base-protected and protected on the morpholino nitrogen, (Structure 1, FIG. 11) is dissolved in 5 ml of dichloromethane. Six mmole of N-ethylmorpholine and 2 mmole of dimethylaminodichlorophosphate ($O=P(Cl)_2N(CH_3)_2$) for Y=O (or the thiophosphate analog for Y=S) are added, followed by the addition of 0.5 mmole of N-methylimidazole. After the reaction is complete (assessed by thin layer chromatography), the reaction solution is washed with aqueous $NaH_2PO_4$. The solution is then fractionated on a silica gel column developed with acetone/chloroform (1:4, v/v) to give the activated subunit (Structure 2, FIG. 11, where X is —$N(CH_3)_2$). As in Exampled 8A, this activated subunit is then added to a DMF solution containing a second subunit having a free morpholino nitrogen (Structure 3); this reaction yields the dimer shown as Structure 4.

The dimethylaminodichlorophosphate (X is —$N(CH_3)_2$ and Y is oxygen) used in the above procedure was prepared as follows: a suspension containing 0.1 mole of dimethylamine hydrochloride in 0.2 mole of phosphorous oxychloride was refluxed for 12 hours and then distilled (boiling point is 36° C. at 0.5 mm Hg). The dimethylaminodichlorothiophosphate (X is —$N(CH_3)_2$ and Y is sulfur) used above was prepared as follows: a suspension containing 0.1 mole of dimethylamine hydrochloride in 0.2 mole of thiophosphoryl chloride was refluxed for 18 hours and then distilled (boiling point 85° C. at 15 mm Hg).

EXAMPLE 9

Activation and Coupling To Give Amide Linkage

This example describes the activation of the carboxylate subunit, prepared in Examples 3 and 4A (wherein the ring is closed on glycine), and its coupling reaction to form an amide linkage. This example is described with reference to the Structures in FIG. 12.

Activation 10 mmole of the carboxylate subunit (Structure 1), prepared in Examples 3 and 4A is dissolved in 100 ml of DMF containing 20 mmole of p-nitrophenol and 15 mmole of dicyclohexylcarbodiimide. After 1 hour the solution is rotovaped dry and the resulting product purified by silica gel chromatography eluted with chloroform/methanol (Structure 2).

Deprotection

Eleven mmole of the carboxylated subunit (Structure 1), prepared in Examples 3 and 4A, is dissolved in 100 ml of dichloromethane ($CH_2Cl_2$) containing 1 ml of dichloroacetic acid. After 5 minutes the $CH_2Cl_2$ is removed under reduced pressure and the product washed with ether. The product is then dried and dissolved in 50 ml DMF containing 1 ml triethylamine to give the product shown as Structure 3.

Coupling

The activated subunit (Structure 2) is added to the DMF solution containing the deprotected subunit (Structure 3) and incubated at room temperature for 1 hour to give the coupled product shown as Structure 4.

EXAMPLE 10

Activation and Coupling to Give Sulfonamide Intersubunit Linkage (F—F)

This example describes the activation and coupling of sulfonic acid subunits prepared as in Examples 3 and 4A (wherein the ring is closed on aminomethanesulfonic acid). The example is described with reference to structures in FIG. 13.

Activation

Ten mmole of the triethylamine salt of sulfonate subunit (Structure 1 of FIG. 13) prepared as described in Examples 3 and 4A, base-protected and protected on the 5' nitrogen, is dissolved in 100 ml of dichloromethane. To this solution, 40 mmole of pyridine is added. This solution is chilled 15 minutes on a bed of dry ice and then 1.1 mmole of phosgene (20% in Toluene) is added. Following addition of the phosgene, the solution is allowed to come to room temperature. The solution is then washed with aqueous $NaHCO_3$, dried, and the sulfonyl chloride (Structure 2 of FIG. 13) isolated by silica gel chromatography using chloroform/20% acetone.

Deprotection

Eleven mmole of the triethylammonium salt of sulfonate subunit (Structure 1 of FIG. 13) is dissolved in 100 ml of trifluoroethanol, followed by the addition of 1 ml formic acid. After 4 minutes the solution is concentrated under reduced pressure and the deprotected subunit (Structure 3 of FIG. 13) precipitated with ether. The precipitate is washed thoroughly with ether and resuspended in 50 ml of DMF containing 5 ml of triethylamine.

Coupling

The activated subunit (Structure 2) is added to the DMF solution containing the deprotected subunit (Structure 3) and incubated at room temperature for 1 hour. This reaction yields the coupled product shown as Structure 4.

EXAMPLE 11

Activation and Coupling to Give Phosphonamide Intersubunit Linkage

This example describes the formation of a phosphonamide linkage. The example is described with reference to structures in FIG. 14.

Activation

Ten mmole of subunit (Structure 1), prepared as in Examples 3 and 4A (wherein the ring is closed on aminomethane phosphonic acid), is dissolved in 100 ml of methanol containing 20 mmole of triethylamine. 20 mmole of dicyclohexylcarbodiimide is added and the solution is stirred for one hour. Methanol is removed under reduced pressure and the product (Structure 2) is purified by silica gel chromatography developed with a chloroform/20% acetone mixture 1% in triethylamine.

Five mmole of the resulting phosphonate ester (Structure 2) is dissolved in 50 ml of chloroform and shaken with aqueous pyridine hydrochloride. The chloroform layer is rotovaped and the remaining solid resuspended in acetonitrile. The solvent is then removed under reduced pressure and the solid is dried overnight under high vacuum. The product (pyridinium salt of Structure 2) is dissolved in 50 ml of chloroform. To this solution 10 mmole of DCC and 10 mmole of triazole (dry) are added and the reaction mix stirred one hour. The chloroform is removed under reduced pressure until precipitation just begins, at which time ten volumes of hexanes are added. The solid (Structure 3) is triturated with hexane to remove any residual carbodiimide.

Deprotection

The remaining 5 mmole of the phosphonate ester (Structure 2) is suspended in 2% formic acid in trifluoroethanol and stirred five minutes. The solvent is removed under reduced pressure and the product (Structure 4) triturated with ether.

Coupling

The deprotected subunit (Structure 4) is dissolved in 50 ml of DMF followed by the addition of the activated subunit (Structure 3) to the reaction mixture. This mixture is incubated at 37° C. for 2 hours to give the dimer shown as Structure 5.

EXAMPLE 12

Solution-Phase Block Assembly of Phosphordiamidate-Linked Oligomer of the Sequence 5'-CUGU This example describes the assembly of a short oligomer containing a phosphordiamidate-linked backbone (Structure D—D D of FIG. 4, where X is $-N(CH_3)_2$ and Z is oxygen) coupled as in Example 8c. This solution assembly method is particularly useful for large-scale synthesis of short oligomers suitable for subsequent assembly into longer oligomers using the solid-phase method (Example 13).

5'OH morpholino subunits of C, U, and G protected on the morpholino ring nitrogen are prepared as in Example 3. The U subunit is then activated by conversion to the monochlorophosphoramidate form as in Example 8C. The C subunit and the G subunit are deprotected with trifluoroethanol containing 2% acetic acid which is then removed under reduced pressure. The residue is washed with ether to remove any residual acetic acid. The deprotected C component (1.1 m mole) is dissolved in 5 ml DMF and 0.3 ml TEA, followed by addition of 1.0 m mole of the activated U component. Likewise, the deprotected G component is reacted with the activated U component.

After one hour each of these preparations is added to 100 ml of rapidly stirred brine and the solid collected and washed with water. The GU dimer is dried thoroughly under high vacuum and then activated as in Example 8c. The best tetramer coupling results are obtained when purification of the dimer, via silica gel chromatography, is carried out after, rather than before, this activation step.

The CU dimer is deprotected as above. Better yields of tetramer are obtained when the dimer, after the initial ether precipitation, is thoroughly resuspended in about 2 ml of trifluoroethanol, reprecipitated with 30 ml of ether, and then resuspended in DMF and TEA for subsequent coupling.

Coupling to form the desired tetramer entails simply adding 1 m mole of activated GU dimer to the DMF/TEA solution containing 1.1 m mole of deprotected CU dimer.

Workup of the tetramer entails adding the reaction mixture to brine, washing the solid with water, and drying under vacuum to give the desired tetramer: 5'-CUGU having a hydroxyl at the 5' end and a protective group on the morpholino nitrogen of the terminal U subunit. The structure of this tetramer is most easily confirmed by negative ion Fast Atom Bombardment mass spectroscopy. As a rule the dominant species in the spectrum is the molecular ion.

EXAMPLE 13

Solid-Phase Assembly of Phosphordiamidate-Linked Morpholino Polymer

This example describes the use of tetramer blocks, prepared as per Example 12, for solid-phase assembly of a morpholino polymer containing phosphordiamidate intersubunit linkages. Solid-phase assembly provides a rapid method for assembly of longer binding polymers. The use of short oligomer blocks instead of monomers greatly simplifies separation of the final product from failure sequences.

A. Synthesis of Short Oligomers

The following tetrameres are synthesized in solution: 5'-CUGU (Example 12); 5'-UCGG; 5'-GCGC; 5'-CACU. These tetrameres are converted to their activated monochloro form by the general method described in Example 8C.

B. Preparation of the First Monomer with a Cleavable Linker and Attachment to the Solid Support Morpholino C subunit containing a protective group on the morpholino ring nitrogen and having a methylamine on the 5'methylene, prepared as in Example 4A, is reacted with a 3-fold molar excess of Bis[2-(succinimidooxycarbonyloxy)ethyl]sulfone from Pierce of Rockford, Ill., U.S.A. This product is purified by silica gel chromatography and then added to a suitable solid support containing primary amine product is purified by silica gel chromatography and then added to a suitable solid support containing amine functions (e.g., Long Chain Alkyl Amine Controlled Pore Glass, from Pierce of Rockford, Ill.). This procedure links the first protected subunit to the synthesis support via a linker which is stable to the acidic conditions used for deprotection of the morpholino nitrogen, but which can be readily cleaved via a beta elimination mechanism using a strong non-nucleophilic base, such as a 1,8-Diazabicyclo[5.4.0]undec-7-ene (DBU).

C. Stepwise Assembly of the Polymer Bound to the Solid Support

The coupling cycle for addition of each subunit or oligomer block generally includes deprotection of the terminal backbone moiety, a thorough wash, addition of the next activated subunit or oligomer block, and a thorough wash. The coupling efficiency for each addition can be determined by collecting each deprotection solution and subsequent wash and quantitating the 4,4'-dimethoxybenzhydryl (DMB) therein.

Deprotection in the present polymer is achieved by slowly passing through the column a solution of 2% acetic acid in trifluoroethanol until the eluant no longer tests positive for dimethoxybenzhydryl (readily determined by adding a drop of eluant to 100 μl methanesulfonic acid and inspecting for the visible color characteristic of the carbonium ion). Thereafter the support is thoroughly washed to remove excess acid and then washed with DMF containing 1% by volume of N-ethylmorpholine (NEM). Coupling of the next subunit or oligomer block in the desired polymer sequence entails addition of a concentrated DMF solution containing the activated monomer or oligomer and a molar equivalent of NEM. Since the rate of coupling is a function of concentration it is desirable to add a substantial molar excess of monomer or oligomer relative to the concentration of support-bound growing chains. A 5-fold molar excess of activated monomer or oligomer over that of the growing chains often gives acceptable coupling efficiencies. Required coupling times can be determined by removing at specified time intervals small defined quantities of the support material, thoroughly washing, treating the support with methanesulfonic acid, and then spectrophotometrically quantitating the released carbonium ion. After coupling is complete the unreacted subunit or oligomer is washed from the support with DMF. The unreacted subunit is generally recovered, purified by chromatography, and reused for later synthesis. The support is thoroughly washed with the solvent trifluoroethanol, without added acid. Washing is complete when addition of a drop of the wash eluant to 100 μl methanesulfonic acid shows no color.

The above coupling cycle is used to add, in order, the four activated tetrameres 5'-CUGU; 5'-UCGG; 5'-GCGC; and 5'-CACU This results in the following polymer: support-linker-CCUGUUCGGGCG-CCACU-DMB.

D. Cleavage from the Support

The synthesis support is treated with 20% DBU in DMF for two hours at room temperature in the presence of 2% diethylmalonate, to tie up the vinylsulfone generated during cleavage of the linker. The released morpholino polymer is washed from the support with DMF and precipitated by adding ethylacetate. The precipitate contains full-length polymer having a 5' methylamine, the bases still protected and a DMB moiety on the terminal morpholino nitrogen. In addition, the precipitate contains small amounts of failure sequences. At this stage the polymer size can be confirmed by positive ion fast atom mass spectrometry.

E. Addition of Solubilizing Moieties

If it is desired to add two solubilizing groups to the morpholino polymer this can be done conveniently by deprotecting the N-terminal morpholino nitrogen using 2% acetic acid in trifluoroethanol. Alternatively, if only one solubilizing moiety is to be added, then the 5'methylamine is acetylated with acetic anhydride before the deprotection step.

Polyethylene glycol 1000 (from Polysciences Inc., Warrington, Pa., U.S.A.) is thoroughly dried by dissolving in dry DMF and then evaporating the solvent under vacuum. The solid is resuspended in a minimal volume of pure dry DMF and 0.5 mole equivalent (relative to PEG 1000) of bis(p-nitrophenyl)carbonate and 1 mole equivalent of TEA is added and the preparation sealed and incubated overnight at 30° C. to give p-nitrophenyl carbonate-activated PEG 1000.

The full-length morpholino polymer which has been deprotected is added to a substantial molar excess (generally 10- to 20-fold) of activated PEG 1000 and incubated two hours at room temperature. Unreacted PEG 1000 is removed by precipitation of the tailed polymer with ether.

F. Base Deprotection

The dried polymer is suspended in DMSO, the DMSO solution chilled, and an equal volume of concentrated $NH_4OH$ is carefully layered on top of the chilled DMSO, and the container tightly capped. The preparation is incubated at 30° C. for eighteen hours. Thereafter, the solution is briefly exposed to aspirator vacuum to remove ammonia.

G. Purification of Morpholino Polymer

Purification at pH 2.5 is general for binding polymers where about half or more of the base-pairing moieties are of types 1, 2, 3, and 7 of FIG. 2.

Water to be used for chromatography is degassed under aspirator vacuum and phosphoric acid added to give pH 2.5 (solvent A). A corresponding pH 2.5 solution is made 2N in KCl (solvent B). Solvent A is mixed 1:1 by volume with chromatographic-grade acetonitrile to give (solvent C).

Load up to about 10 mg of this polymer in 10 ml of solvent A on a chromatography column 1 cm in diameter and 10 to 20 cm in length which is packed with the cation-exchange support S-Sepharose Fast Flow (Pharmacia). Proportionately larger quantities can be loaded on larger columns of the same length, e.g., up to 60 mg can be loaded on a 2.5 cm diameter column and 250 mg on a 5 cm diameter column. After washing the column thorough with solvent A elute with a linear gradient ranging from 100% solvent A to 100% solvent B and monitor the eluant to 254 nm. The desired binding polymer is generally the last and the largest peak to elute from the column. When the polymer is prepared by block assembly, base-line separations are often achieved. When peak shapes are unsymmetrical the problem generally has been due to insolubility of the binding polymer rather than a lack of capacity of the chromatographic packing. Such a problem, which is most common when the binding polymers do not contain a solubilizing moiety, can often be solved by reducing the quantity of binding polymer loaded in a given run. When peaks are symmetrical but base-line separation is not achieved, substantial improvements are usually attained simply by eluting with a shallower gradient.

The eluant containing the polymer is desalted by loading on an equivalent-sized column packed with 35 micron chromatographic polypropylene (Cat. No. 4342 from Polysciences, Inc.) and washing thoroughly with solvent A. If baseline separation was achieved in the foregoing cation exchange chromatography, then pure product is obtained simply by eluting with solvent C; otherwise, the product is eluted with a linear gradient ranging from 100% solvent A to 100% solvent C. When the product is somewhat acid sensitive the solution is neutralized with dilute NaOH before drying under reduced pressure.

Purification at High pH

Purification at pH 11 is generally used for binding polymers where above half or more of the base-pairing moieties are at type 4, 5, 6 and 9 of FIG. 2.

N,N-diethylethanolamine (Aldrich) is added to degassed water to adjust the pH to 11.0 (solvent D). A corresponding pH 11 solution 2N in KCl (solvent E) is prepared. A third pH 11 solution is prepared by mixing Solvent D 1:1 by volume with chromatographic grade acetonitrile (solvent F).

The fully-deprotected binding polymer, prepared as above, is suspended in solvent D at a concentration of about 1 μg/ml. The pH is adjusted, if necessary, to pH 11 with N,N-diethylethanol-amine. About 10 ml of this polymer solution is placed on a chromatography column 1 cm in diameter and 10 to 20 cm in length which is packed with anion-exchange support Q-Sepharose Fast Flow (Pharmacia). After washing the column thoroughly with solvent D, the column is eluted with a linear gradient ranging from 100% solvent D to 100% solvent E and the eluant is monitored at 254 nm.

The eluant containing the polymer is desalted by loading on an equivalent-sized column of polypropylene and washing thoroughly with solvent D. If baseline separation is achieved in the foregoing anion exchange chromatography then pure product is obtained simply by eluting with solvent F; otherwise, the product is eluted with a linear gradient ranging from 100% solvent D to 100% solvent F. Fractions containing the product are dried under reduced pressure.

H. Sequence Confirmation

While mass spectral analysis of the full-length polymer in the fully-protected state, as described earlier, does serve to confirm both the polymer length and the base composition, it does not provide information on the subunit sequence. Significant sequence information can be obtained from fragmentation patterns of deoxyribonucleic acids and carbamate-linked deoxyribonucleoside-derived polymers (Griffin et al. (1987), Biomed. & Environ. Mass Spectrometry 17:105); however, many of the morpholino polymers of the instant invention are quite resistant to fragmentation and give predominantly the molecular ion with only minimal fragments.

One method for confirming the sequence of the polymer is to take a small portion of the growing polymer after coupling each oligomer block and use mass spectral analysis to follow the elongation of the polymer. This method is applicable except for those rare cases where two blocks used in the synthesis happen to have exactly the same mass.

An indirect method to help verify the correctness of the polymer subunit sequence is to pair the morpholino polymer with its complementary DNA (whose sequence can be confirmed by established methods) and with DNA sequences which might have resulted if the blocks were assembled in the wrong order. Pairing between the polymer and DNA can be evaluated by assessing for a hypochromic shift in the 240 to 290 nm wavelength region. Such a shift occurs only between the polymer and its complementary sequence. The polymer/DNA duplex can also be distinguished from any partially-mismatched duplex by slowly raising the temperature while monitoring the absorbance in the 240 to 290 nm wavelength region. The perfect duplex will have a melting temperature (corresponding to a 50% reduction in the hypochromicity) generally 10 degrees or more above that of any mismatched duplex.

While specific embodiments, methods, and uses of the invention have been described, it will be appreciated that various changes and modifications of the invention may be made without departing from the invention. In particular, although preferred polymer backbone structures have been described and illustrated, it will be appreciated that other morpholino-based polymers may be constructed according to the backbone constraints and requirements discussed above.

It is claimed:

1. A polymer composition comprised of α-morpholino subunit structures of the form:

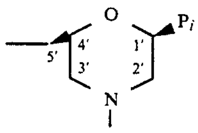

where (i) the structures are linked together by uncharged linkages, one to three atoms long, joining the morpholino nitrogen of one subunit to the 5', exocyclic carbon of an adjacent subunit, and (ii) $P_i$ is a purine or pyrimidine base-pairing moiety effective to bind by base-specific hydrogen bonding to a base in a polynucleotide.

2. The composition of claim 1, wherein $P_i$ is selected from the group consisting of:

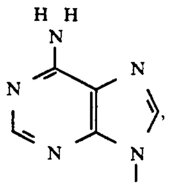

1

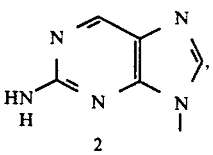

2

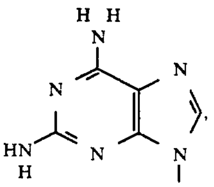

3

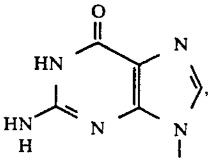

4

-continued

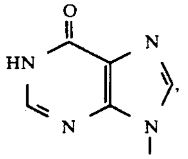

5

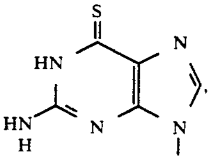

6

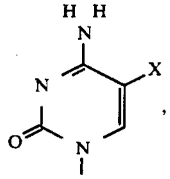

,

7

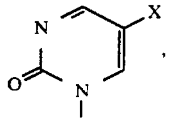

, and

8

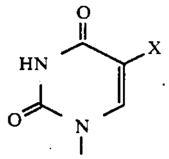

9 where X is H, $CH_3$, F, Cl, Br, or I.

3. The composition of claim 1, wherein the linked structures have a form selected from the group consisting of:

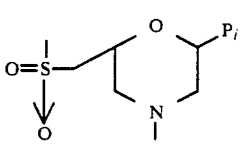

(A)

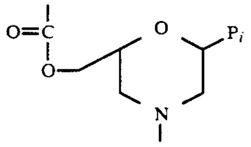

(B)

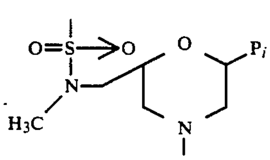

(C)

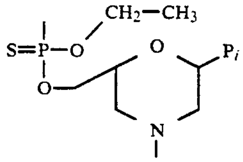

(D)

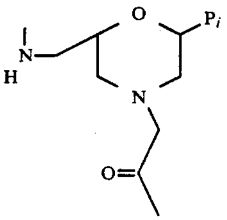

(E)

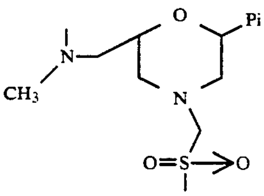

and (F)

-continued

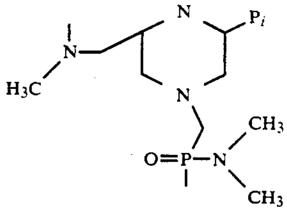

(G)

4. The composition of claim 1, wherein the linkage is of the form:

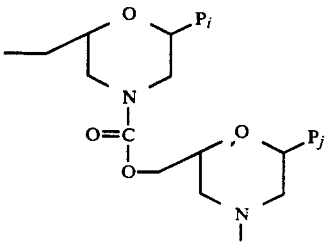

where $P_j$ is a purine or pyrimidine base-pairing moiety effective to bind by base-specific hydrogen bonding to a base in a polynucleotide.

5. The composition of claim 1, wherein the linkage is of the form:

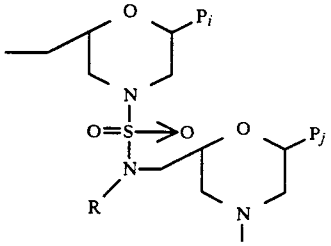

where

R is H, $CH_3$, or other alkyl; and, $P_j$ is a purine or pyrimidine base-pairing moiety effective to bind by base-specific hydrogen bonding to a base in a polynucleotide.

6. The composition of claim 1, wherein the linkage is of the form:

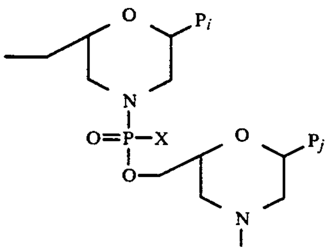

where

X is alkyl, alkoxy, thioalkoxy, or an unsubstituted, monosubstituted, or disubstituted nitrogen; and, $P_j$ is a purine or pyrimidine base-pairing moiety effective to bind by base-specific hydrogen bonding to a base in a polynucleotide.

7. The composition of claim 1, wherein the linkage is of the form:

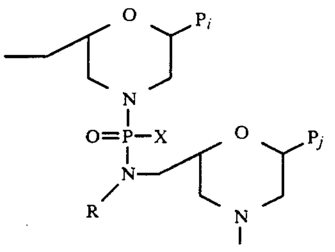

where

X is alkyl, alkoxy, thioalkoxy, or an unsubstituted, monosubstituted, or disubstituted nitrogen;

R is H or $CH_3$; and $P_j$ is a purine or pyrimidine base-pairing moiety effective to bind by base-specific hydrogen bonding to a base in a polynucleotide.

8. The composition of claim 1, wherein the linkage is of the form:

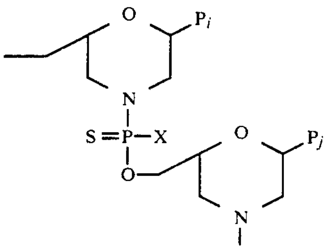

where

X is alkyl, alkoxy, thioalkoxy, or an unsubstituted, monosubstituted, or disubstituted nitrogen; and, $P_j$ is a purine or pyrimidine base-pairing moiety effective to bind by base-specific hydrogen bonding to a base in a polynucleotide.

9. The composition of claim 1, wherein the linkage is of the form:

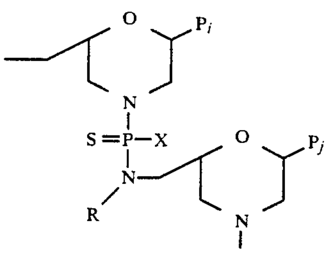

where

X is alkyl, alkoxy, thioalkoxy, or an unsubstituted, monosubstituted, or disubstituted nitrogen;

R is H or $CH_3$; and $P_j$ is a purine or pyrimidine base-pairing moiety effective to bind by base-specific hydrogen bonding to a base in a polynucleotide.

10. The composition of claim 1, wherein the linkage is of the form

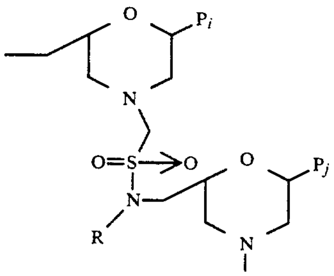

where

R is H or $CH_3$, or other alkyl; and $P_j$ is a purine or pyrimidine base-pairing moiety effective to bind by base-specific hydrogen bonding to a base in a polynucleotide.

11. The composition of claim 1, which further includes a moiety at one or both termini which is effective to enhance the solubility of the polymer in aqueous medium.

12. The composition of claim 11, wherein the terminal moiety is polyethylene glycol.

13. The composition of claim 1, composed of at least 3 morpholino subunits.

14. The composition of claim 1, wherein at least one of the $P_i$ is a 2,6-diaminopurine.

15. The composition of claim 1, wherein at least one of the $P_i$ is a 5-halouracil.

16. The composition of claim 1, wherein at least 70% of the $P_i$ are 2-amine containing purines.

* * * * *